United States Patent [19]

Gross

[11] 4,097,586

[45] Jun. 27, 1978

[54] IMMUNOCHEMICAL ASSAY METHOD

[75] Inventor: Stanley Joseph Gross, Encino, Calif.

[73] Assignee: Biological Developments, Inc., Encino, Calif.

[21] Appl. No.: 658,180

[22] Filed: Feb. 17, 1976

Related U.S. Application Data

[60] Continuation-in-part of Ser. No. 160,559, Jul. 7, 1971, Pat. No. 3,940,475, and Ser. No. 462,517, Apr. 19, 1974, said Ser. No. 160,559, is a division of Ser. No. 89,929, Nov. 16, 1970, abandoned, which is a continuation-in-part of Ser. No. 45,558, Jul. 11, 1970, abandoned, said Ser. No. 462,517, is a continuation-in-part of said Ser. No. 89,929, which is a continuation-in-part of said Ser. No. 45,558.

[51] Int. Cl.$^2$ .................. A61K 43/00; G01N 33/00; G01N 33/16
[52] U.S. Cl. .................... 424/1; 23/230 B; 424/12
[58] Field of Search .............. 424/111.5, 112; 23/230 B

[56] References Cited

U.S. PATENT DOCUMENTS 3,940,475  2/1976  Gross ........................ 424/1

Primary Examiner—Benjamin R. Padgett
Assistant Examiner—Christine M. Nucker
Attorney, Agent, or Firm—McAuley, Fields, Fisher & Goldstein

[57] ABSTRACT

Haptens and antigen derivatives are coupled, through an azo bond, to proteins to form a conjugated material. The conjugate is injected into laboratory animals to raise antibodies which are useful in immunochemically assaying for the original haptens and antigen derivatives. Included among the immunochemical assay methods are radio-immune assays and fluorescence methods.

22 Claims, No Drawings

IMMUNOCHEMICAL ASSAY METHOD

CROSS-REFERENCE TO RELATED APPLICATIONS

This application is a continuation-in-part of my copending application Ser. No. 160,559, filed July 7, 1971, for "Hapten and Antigen Derivatives and Methods for their Preparation," now U.S. Pat. No. 3,940,475, which is a division of my application Ser. No. 89,929, filed Nov. 16, 1970, which, in turn, was a continuation-in-part of my application Ser. No. 45,558, filed July 11, 1970, the latter two applications now being abandoned; this application is also a continuation-in-part of my copending application Ser. No. 462,517, filed Apr. 19, 1974 for "Hapten and Antigen Derivatives and Methods for Their Preparation," which was a continuation-in-part of my aforereferenced application Ser. No. 89,929 which, in turn, was a continuation-in-part of my aforereferenced application Ser. No. 45,558.

BACKGROUND OF THE INVENTION

This invention relates to hapten-protein conjugates and to their use in immunochemical assays, including radioimmune and fluorescent assays.

An important problem in medicine is the detection and characterization of small amounts of metabolically significant substances, e.g., steroids, the catecholamines, insulin, and polypeptides, in body fluids and cells. Current methods lack sensitivity as well as specificity for the substance under assay. The results of such assays are therefore unreliable.

The importance of reliable assay methods is illustrated by the steroids, estradiol and estriol, which have a known significance in fetal abnormalities.

The fetus produces, predominantly from its adrenal gland, an androgenic molecule which serves as the precursor for estriol and is the major source for the latter in maternal serum. It is the placenta, which is a fetal product predominantly, which aromatizes the precursor molecule and hydroxylates it, resulting in estriol.

The levels of estriol in maternal blood and urine are markedly increased during pregnancy as a result of the metabolic changes. This is normal. At least one thousand to ten thousand fold increase in estriol levels occurs at term gestation, if the pregnancy is normal. However, if the fetus is in distress or is diseased, or if the placenta is immature or markedly diseased and the fetus in danger of dying, estriol levels in the maternal serum are diminished. This is true also if there is diminution of estriol in the maternal urine (assuming normal renal function) or fetal amniotic fluid.

As a result, an accurate, rapid measure of estriol levels in these body fluids would be useful in predicting fetal survival and in enabling the attending physician to judge when it may be desirable to perform a Caesarian section or to treat the mother in other fashion to save the fetus.

Estradiol is the most active of the estrogenic materials during gestation. The full impact of estradiol (and for that matter estrone) in the mother remains unknown because levels have not been accurately determinable.

For the same reason, pregnancy levels of individual estrogens from conception to 8 weeks of gestation are not known because present technology does not permit accurate determination. If such determination were possible from the earliest days of conception, a standard curve could be drawn and an earlier and more reliable test for pregnancy made available.

A relatively new approach to biological assaying involves immunochemical procedures as a basis for the assay. Such procedures involve the attempted production of a synthetic antigen* which produces antibodies specific for the compound to be assayed. A known amount of such antibody and the unknown, (for example, steroid) sample, obtained from the test species, are intermixed. Theoretically, if the antibody were specific for the steriod one could then measure the amount of antibody reacting with the steroid. This amount could then be translated into the amount of test steroid present, assuming, or course, that the method of measurement was sufficiently at the concentrations involved.

*A molecule which generates antibodies in a host, e.g. bovine serum albumin.

Unfortunately to date no immunochemical technique has been developed which produces a reliable, accurate assay. A significant problem with previous immunochemical approaches, aside from the lack of sensitivity of availble measurement techniques, has been that the synthetic antigen does not produce an antibody which is specific for the test steroid. For example, a paper published in Immunochemistry 5, 55–65 (1968) described the synthesis of certain steroidprotein conjugates and the production of rabbit antiserum to beta-estradiol, coupled to bovine serum albumin (BSA) and keyhole limpet hemocyanin (KLH). Antisera were tested against steroids coupled to human gamma globulin (IgG). The immunological assays employed quantitative precipitin and hapten inhibition tests.

The conjugates produced in accordance with the method described in this paper did not produce antibodies which were specific for the steroid hapten (i.e. beta-estradiol, estriol and estrone) employed in the conjugate. Antibody to estradiol-KLH brought down a nonspecific precipitate with testosterone-IgG, and antibody to estriol-KLH brought down a precipitate (nonspecifically) with testosterone-IgG and with estradiol-IgG. Thus, it is impossible to achieve accurate assays employing the antibodies produced according to this method.

As will become apparent from the following description, a unique, simple, yet extremely reliable immunochemical assaying method, including fluorescent and radio-immune assays for a wide variety of metabolically significant substances including estrone, estradiol, estriol, the catecholamines and insulin and most polypeptides is provided.

SUMMARY OF THE INVENTION

In accordance with one embodiment of this invention, there are provided novel antigens, such as steroid-protein antigens, catecholamine-protein antigens and others more fully described hereafter. Upon injection of these antigens in their pure form into antibody-producing host, antibodies specific for the corresponding metabolically active substance (e.g. the steroid or catecholamine) are produced. These antibodies give precise and accurate results when employed in fluorescent and radioimmune assays for such substances. Such antibodies and assays form embodiments of this invention. Injection of such antigens into the host is another embodiment, forming a useful method for immunizing the host against, or destroying in the host, the physiologic function of the corresponding metabolites.

Also embodied in this invention are novel processes and intermediates useful in producing the foregoing antigens and antibodies, as well as processes for the preparation thereof in their pure form. In addition novel fluorescent hapten and antigen derivatives useful in the fluorescent assay form a further embodiment, as do processes for their preparation. These and other embodiments of this invention will be apparent from the following detailed description.

DETAILED DESCRIPTION OF THE INVENTION

The steroid-protein antigens of this invention are represented by the following structural formula:

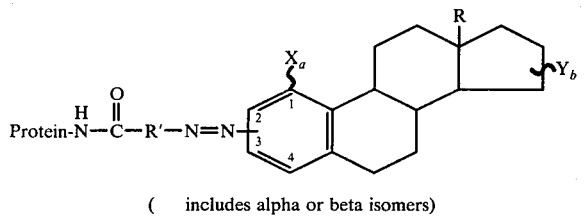

( includes alpha or beta isomers)

wherein R is hydrogen, or lower-alkyl ($C_1$–$C_4$); R' is any moiety capable of sustaining a diazonium ion*, such as an unsubstituted arylene, preferably phenylene or naphthylene, containing from about 6 to about 14 carbons; or a substituted arylene containing 1-3 groups which do not interfere with the formation of a diazonium ion (i.e. sustained by the aryl amine moiety, —R'$NH_2$)preferably those groups selected from the following: amino, nitro, halo, (i.e. chloro, bromo, fluoro, iodo), $HSO_3$, carboxyl, or a fused ring moiety such as naphthyl or terphenyl; X is hydrogen or a radical selected from hydroxy, keto, ester (—OR wherein R is alkyl or cycloalkyl, preferably $C_1$–$C_4$, aryl, preferably $C_6$–$C_{10}$, and includes adamantyl); primary, secondary, or tertiary amino (—$NH_2$, —NHR", —$NR_2$"); lower-alkyl; halo; aryl, preferably $C_6$–$C_{10}$; alkenyl; -N=NR"; —SC≡N; —OOCR"; —NHCOR"; —SR"; —SOR"; —NO and the like ortho or para directing roups; —$NO_2$; carboxyl; —COOR"; —$SO_3H$; —$CF_3$; —$CCl_3$; —$NR_3$" ⊕; —CN; —COR"; —$SO_3R$"; —$IO_2$; —R"λ (OH)$_2$ and the like meta directing groups. R" is alkyl, cycloalkyl, aryl, alkenyl, cycloalkenyl, heterocyclic wherein the hetero atoms are O, S or N. R" preferably contains from about 1 to about 10 carbons in the aliphatic chains and from about 4 to about 14 ring atoms in the cyclic groups. Y can be the same as X and, additionally, can be any organic or inorganic substituent which is stable under the conditions utilized in the synthesis of the novel steroid-protein conjugates of this invention. The letters $a$ and $b$ designate a whole integer from 1 through 3.The protein carrier moiety can be any heavy protein having a molecular weight of greater than about 6000. The protein moiety must be immunogenic and preferably heterologous. Exemplary of such proteins are keyhole limpet hemocyanin (KLH, molecular weight approximately 7 million), bovine serium albumin (BSA, molecular weight 70,000) and human gamma globulin (IgG, molecular weight 150,000) Reference to "Structural Concepts in Immunology and Immunochemistry" (Elvin Kabat published by Holt, Rinehart & Winston (1968) pages 9-26) disclose other proteins or carrier molecules which can be employed in this invention. Furthermore the protein moiety in the foregoing formula can be replaced with polysaccharides, polypeptides or glyco proteins containing carboxyl hydroxyl or amino groups suitable for coupling with the azosteroid intermediates of this invention. These immunogenic substances are set forth in Cremer N.E. et al, Methods In Immunology (1963), W.A. Benjamin Inc., N.Y. pp. 65-113. Again such moieties must be immunogenic and generally have a molecular weight greater than about 6000. These immunogenic substances are further illustrated in Kabat, supra. The term "protein" as used herein is meant to encompass these other immunogenic substances.

*e.g. see P.A. Smith, The Chemistry of Open Chain Nitrogen Compounds, Vol. 1, pp. 100-105, W. A. Benjamin N.Y. 1965.

In the foregoing formula it is preferred for X to be OH and a 1. X is preferably substituted at the 3 position of the steroid (alpha or beta). The azo moiety is therefore substituted at the 2 or 4 position of the steroid (alpha or beta). R preferably is methyl or hydrogen in the alpha or beta configuration. It is preferred that Y be OH or keto. When Y is OH, $b$ is preferably 1 or 2, and Y is substituted at the 16 and 17 position (alpha or beta) of the steroid, usually in the 16 alpha and 17 beta configuration. When Y is keto, $b$ is 1 and substitution is at the 17 position. The protein is preferably KLH, IgG, or BSA, as discussed above.

In the foregoing formula X is defined as an $o$, $m$ or $p$ directing group. However, X can also be hydrogen. In such cases more rigorous reaction conditions are employed.

The novel antigenic compounds represented by the above formula and those discussed hereafter possess useful pharmacological properties. In particular, these compounds in their pure form have been found to be capable of producing antibodies which are absolutely specific for the metabolite corresponding to the hapten moiety of the novel conjugates of this invention. Thus, these antigenic substances are useful in the detection and characterization of minute quantities (e.g. in the 10-20 pikogram range) of metabolites, e.g. steroids, catecholamines, or peptides in body fluids and cells. The results of assays employing antibodies produced by these novel antigenic substances are reliable and accurate.

In producing such antibodies an effective amount (e.g. a total dosage of 30-100 mg per animal) of the haptenprotein antigen is administered in its pure form to an animal preferably a rabbit. It is preferred to administer the antigen every other day intravenously for one week (i.e. three times a week). Two weeks later an effective amount of the antigen with an equal amount of complete Freunds adjuvant is administered subcutaneously (once only). Three weeks later the animal is bled and the antibody contlained in the blood serum is separated using conventional techniques. Exemplary is the administration of 0.5, 0.75, or 1.0 ml of 1% (by weight of protein) aqueous solution of estradiol-KLH intravenously thrice weekly for 2 weeks, followed by 2.5 ml of 1% solution in an equal volume of Freunds adjuvant, subcutaneously.

The antigens represented by the above structural formula can be prepared according to the following reaction sequence I:

REACTION SEQUENCE
(~ includes alpha or beta isomers)

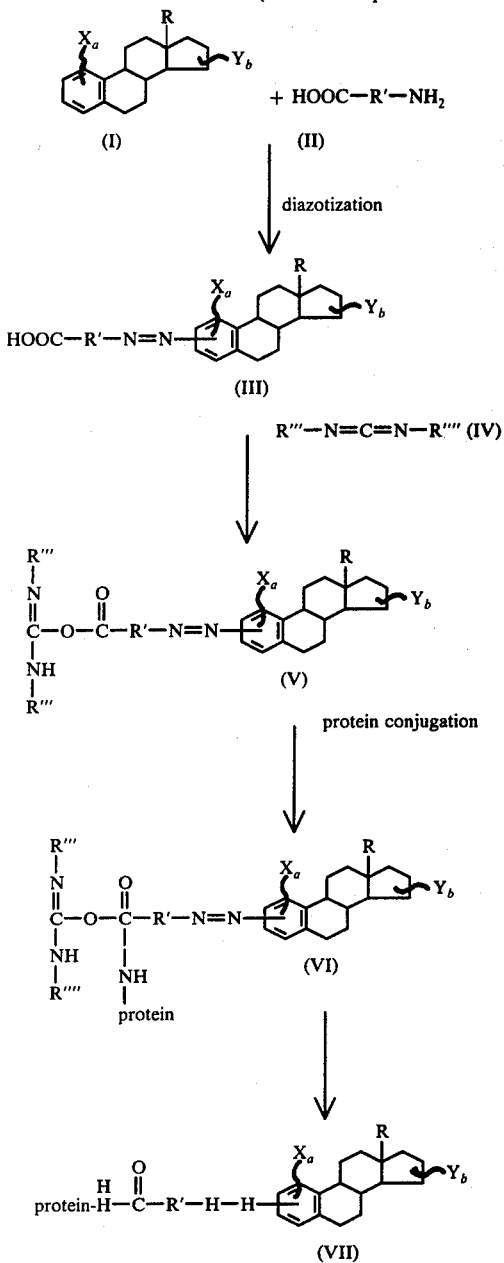

wherein the definitions of R, R', X, Y, a and b are as previously defined. R" and R'" and R"" are the same or different and can be alkyl, e.g. lower-alkyl; cycloalkyl, e.g. of 4–8 carbons; aryl, e.g. 6–10 carbons; alkenyl, e.g. lower-alkenyl; cycloalkenyl, e.g. monoolefinic of 4–8 carbons, or heterocyclic, wherein the hetero atoms are O, S or N and having 5–7 ring atoms.

Referring to the above reaction sequence, the steroid azo aryloic acid derivative, i.e. the azosteroid, (III) in its pure form is novel and forms an embodiment of this invention. It is prepared from the steroid (I), containing an aromatic A ring, by reaction with an aminoaryloic acid (II) under conventional diazotizing conditions. Generally an excess of nitrous acid is employed. Preferable from about 0.75 equivalent to about 1 equivalent of the amino aryloic acid are employed in the presence of about 0.85 to about 1.2 equivalents of nitrous acid. The diazotization is carried out in a strong mineral acid solution. The nitrous acid is generally generated by the addition of a solution of sodium nitrite to the mixture of the aryl amine in excess mineral acid. Generally the reaction is maintained at a temperature of below 5° C, preferable 0° C. The resulting diazotized amino aryloic acid is added to an approximately equivalent concentration (e.g. 1–1.35) of the steroid (I) resulting in the azosteroid (III). The steroid is generally maintained in a buffered solution having a pH of about 11. The steroid is preferably maintained in an alkanol (e.g. methanol) solution. Esterification with mineral acid, preferably HCl, results in the precipitation of the desired azosteroid (III) in crude form.

The crude azosteroid is a sterioisomeric mixture and contains other reaction by-products. Which isomer is predominantly produced depends upon the substituent X (both as to its character and site) in the foregoing reaction sequence. The purification of the predominate azosteroid (III) isomer is carried out using chromatographic techniques. For example, the azosteroid can be chromatographed on a column of silica gel to produce the desired azosteroid (III) in substantially pure form, i.e. greater than about 98% pure.

The pseudourea coupling intermediate (V) forms a novel embodiment of this invention and is produced by reacting the pure azosteroid (III) with the carbodiimide (IV). Temperatures are not critical and generally range from about −10° C to about 25° C. The reaction is carried out in aqueous solution, preferably 1% aqueous saline solution. It is preferred to react the azosteroid (III) and carbodiimide (IV) in the presence of the conjugating protein (e.g. KLH, IgG, or BSA). Generally the protein is added to a mixture of the other ingredients.

The novel intermediate pseudoureas (V) are preferably isolated before conjugation with protein carriers in high (10) pH/20% methanol. After freeze drying the pseudourea is reacted with proteins in the desired molar ratio (e.g. 10–30:1). This approach has the desirable advantage of preventing protein polymerization by free carbodiimide.

Protein conjugation occurs at temperatures ranging, as above, from about −10° C to about 25° C, but can range as high as 60° C. Aqueous reaction mixtures are employed. Conjugation proceeds through the intermediate (VI), which is pure and forms an embodiment of this invention, to the desired steroid-protein antigen-(VII).

To couple the azo intermediate (III) to the desired protein, other coupling techniques can be employed, e.g., see Kabat, above, p. 20. For example, the azosteroid (III) can be reacted with a dihalothiocyanate, e.g. dichlorothiocyanate, or with a thionylhalide, e.g. thionyl chloride, to produce stereoisomeric mixtures of the following novel intermediates of this invention:

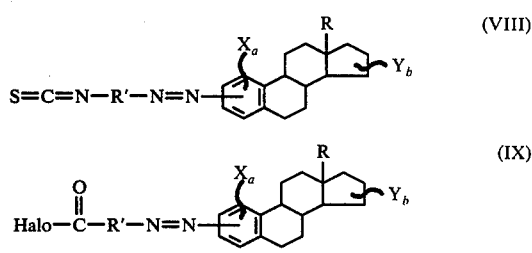

wherein R, R', X, Y, a and b are as defined above. Conjugation of the intermediate (IX) with the protein reactant yields the desired steroid-protein antigen (VII). Conjugation of the intermediate (VIII) with protein yields the following novel antigenic conjugate:

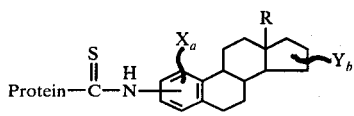     (X)

wherein R, R', X, Y, a and b are as defined above.

EXAMPLE 1

4-(17'BETA-ESTRADIOL-4'-AZO)BENZOIC ACID

A. PREPARATION 0.75 Milliequivalents paraaminobenzoic acid is added to 10 ml of 1N HCl and chilled to 5° C. Add 0.85 milliequivalents sodium nitrite. Stir in ice bath for 20 minutes, pH not exceeding 1. Test with starch-iodide paper, excess nitrite is removed with sulfamic acid. Diazotized paraaminobenzoic acid is added dropwise to an equivalent concentration of estradiol (0.75 milliequivalents) dissolved in 1/10 molar phosphate buffer, pH 11, containing 20% methanol. Additional methanol is added to maintain the steroid soluble. The solution is poured into a beaker containing 20 ml concentrated HCl. It is diluted up to 500 ml. The azosteroid precipitates. After centrifugation it is redissolved in base (0.1M sodium carbonate). Unreacted steroid stays insoluble. After centrifugation the solution is reacidified and extracted into tetrahydrofuran (dried over LiB$_4$) which is evaporated rapidly under nitrogen.

B. PURIFICATION

Crude azoestradiol (250 mg), containing the 4'-azo derivative, some 4-(17'beta-estradiol-2'-azo)benzoic acid and scant 4-(17'beta-estrodiol-1'-azo)benzoic acid, is chromatographed on a 100 g. column of silica gel (Brinkmann, 0.05–0.2mm), packed as a slurry in ethyl acetatel-methanol-water, 98.5:1:0.5. Nonacidic material is first eluted with 400 ml of the same solvent. Elution is continued with ethyl acetate-methanol-acetic acid, 97:2:1. The first 200 ml are discarded and the azoestradiol is collected in the next 300 ml. Evaporation of the solvent gives 67 mg of 4-(17'beta-estradiol-4'-azo)-benzoic acid, about 98% pure by chromatography.

C. PREPARATION OF 4-(17'BETA-ESTRADIOL-4'-HYDRAZO) BENZOIC ACID

Purified 4-(17'beta-estradiol-4'-azo)benzoic acid (25 mg) (0.15 mg/ml), is dissolved in methanol. An eight-fold molar excess of sodium borohydride is added s a solution in water (0.5 mg/ml of azosteroid solution) the mixture being flushed with nitrogen. The reaction mixture (pH 11) is extracted with ethyl acetate which after evaporation, provides 4-aminoestradiol. The pH of the aqueous phase is then lowered to 3-4 which upon extraction and evaporation yields 4-(17'beta-estradiol-4'-hydrazo)benzoic acid. Thin layer partition chromatography yields the desired purified fluorescent 4-aminoestradiol and hydrazoestradiol benzoic acid derivatives.

EXAMPLE 2

4-(17'beta-ESTRIOL-4'-AZO)BENZOIC ACID

A. PREPARATION 0.75 Milliequivalents paraaminobenzoic acid is added to 10 ml 1N HCl and chilled to 5° C. Add 0.85 milliequivalents sodium nitrite. Stir in ice bath for 20 minutes, pH not exceeding 1. Test with starch-iodide paper, excess nitrite is removed with sulfamic acid. Diazotized paraaminobenzoic acid is added dropwise to an equivalent concentration of 17beta-estriol (.75 milliequivalents) dissolved in 1/10 molar phosphate buffer, pH 11, containing 20% methanol. Additional methanol is added to maintain the steriod soluble. The solution is poured into a beaker containing 20 ml concentrated HCl. It is diluted up to 500 ml. The azosteroid precipitates. After centrifugation it is redissolved in base (0.1M sodium carbonate). Unreacted steroid stays insoluble. After centrifugation the solution is reacidified and extracted into tetrahydrofuran (dried over LiB$_4$) which is evaporated rapidly under nitrogen.

B. PURIFICATION

The crude azoestriol from Step A (250 mg), containing the 4'-azo derivative, some 4-(17'beta-estriol-2'-azo)benzoic acid, and scant 4-17'beta-estriol-1'-azo)benzoic acid, is chromatographed on a 100 g. column of silica gel (Brinkmann, 0.025–0.2mm), packed as a slurry in ethyl acetate-methanol-water, 98.5:1:0.5. Non-acidic material is first eluted with 400 ml of the same solvent. Elution is continued with ethyl acetate-methanol-acetic acid, 97:2:1. The first 200 ml are discarded and the azoestriol collected in the next 300 ml. Evaporation of the solvent gives 52 mg of 4-(17'beta'estriol-4'-azo)benzoic acid, about 98–99% pure by chromatography.

C. PREPARATION OF 4-(17'BETA-ESTRIOL-4'-HYDRAZO) BENZOIC ACID

Purified 4-(17'beta-estriol-4'-azo)benzoic acid (25 mg)(0.15 mg/ml) is dissolved in methanol. An eight-fold molar excess of sodium borohydride is added as a solution in water (0.5 mg/ml of azosteroid solution) the mixture being flushed with nitrogen. The reaction mixture (pH 11) is extracted with ethyl acetate which after evaporation, provides 4-aminoestriol. The pH of the aqueous phase is then lowered to 3-4 which upon extraction and evaporation yields 4-(17'beta-extriol-4'-hydrazo)benzoic acid. Thin layer partition chromatography yields the desired purified fluorescent 4-aminoestriol and hydrazoestriol benzoic acid derivatives.

EXAMPLE 3

4-(ESTRONE-4'-AZO)BENZOIC ACID

A. PREPARATION 0.75 Milliequivalents paraaminobenzoic acid is added to 10 ml 1N HCl and chilled to 5° C. Add 0.85 milliequivalents sodium nitrite. Stir in ice bath for 20 minutes, pH not exceeding 1. Test with strarch-iodide paper, excess nitrite is removed with sulfamic acid. Diazotized paraaminobenzoic acid is added dropwise to an equivalent concentration of 17beta-estrone (.75 milliequivalents) dissolved in 1/10 molar phosphate buffer, pH 11, containing 20% methanol. Additional methanol is added to maintain the steroid soluble. The solution is poured into a beaker containing 20 ml concentrated HCl. It is diluted up to 500 ml. The azosteroid precipitates. After centrifugation it is redissolved in base (0.1M sodium carbonate, sodium hydroxide). Unreacted steroid stays insoluble. After centrifugation the solution is reacidified and extracted into tetrahydrofuran (dried over LiB$_4$) which is evaporated rapidly under nitrogen.

B. PURIFICATION

Crude azoestrone (250 mg) containing the 4'-,2'- and 1'-azo stereoisomers is chromatographed on a 100 g. column of silica gel (Brinkmann, 0.05–0.2mm), packed as a slurry in ethyl acetate-methanol-water, 97:2.5:0.5. Non-acidic material is first eluted with 400 ml of the same solvent. Elution is continued with ethyl acetatemethanol-acetic acid, 97:2:1. The first 200 ml are discarded and the azoestrone collected in the next 300 ml. Evaporation of the solvent gives 40 mg of 4-(estrone-4'-azo)benzoic acid, about 98% pure by chromatography.

C. PREPARATION OF 4-(ESTRONE-4'-HYDRAZO) BENZOIC ACID

Purified 4-(estrone-4'-azo)benzoic acid (25 mg) (0.15 mg/ml), is dissolved in methanol. An eight-fold molar excess of sodium borohydride is added as a solution in water (0.5 mg/ml of azosteroid solution) the mixture being flushed with nitrogen. The reaction mixture (pH 11) is extracted with ethyl acetate which after evaporation, provides 4-aminoestrone. The pH of the aqueous phase is then lowered to 3–4 which upon extraction and evaporation yields 4-( estrone-4'-hydrazo)benzoic acid. Thin layer partition chromatography yields the desired purified fluorescent 4-aminoestrone and hydrazoestrone benzoic acid derivatives.

EXAMPLE 4

4-(17'ALPHA-ESTRADIOL-4'-AZO)BENZOIC ACID

A. PREPARATION 0.75 Milliequivalents paraaminobenzoic acid is added to 10 ml of 1N HCl and chilled to 5° C. Add 0.85 milliequivalents sodium nitrite. Stir in ice bath for 20 minutes, pH not exceeding 1. Test with starch-iodide paper, excess nitrite is removed with sulfamic acid. Diazotized paraaminobenzoic acid is added dropwise to an equivalent concentration of 17alpha-estradiol (0.75 milliequivalents) dissolved in 1/10 molar phosphate buffer, pH 11, containing 20% methanol. Additional methanol is added to maintain the steroid soluble. The solution is poured into a beaker containing 20 ml concentrated HCl. It is diluted up to 500 ml. The azosteroid precipitates. After centrifugation it is redissolved in base (0.1M sodium carbonate). Unreacted steroid stays insoluble. After centrifugation the solution is reacidified and extracted into tetrahydrofuran (dried over $LiB_4$) which is evaporated rapidly under nitrogen.

B. PURIFICATION

Crude azoestradiol (250 mg), containing the 4'-,2'- and 1'-azo stereoisomers, is chromatographed on a 100 g. column of silica gel (Brinkmann, 0.05–0.2mm), packed as a slurry in ethyl acetate-methanol-water, 98.5:1:0.5. Non-acidic material is first eluted with 400 ml of the same solvent. Elution is continued with ethyl acetate-methanol-acetic acid, 97:2:1. The first 200 ml are discarded and the azoestradiol collected in the next 300 ml. Evaporation of the solvent give 64 mg of 4-(17'alpha-estradiol-4'-azo)benzoic acid, about 98–99% pure by chromatography.

C. PREPARATION OF 4-(17'ALPHA-ESTRADIOL-4'-HYDRAZO)BENZOIC ACID

Purified 4-(17'alpha-estradiol-4'-azo)benzoic acid (25 mg) (0.15 mg/ml), is dissolved in methanol. An eight-fold molar excess of sodium borohydride is added as a solution in water (0.5 mg/ml of azosteroid solution) the mixture being flushed with nitrogen. The reaction mixture (pH 11) is extracted with ethyl acetate which after evaporation, provides 4-aminoestradiol. The pH of the aqueous phase is then lowered to 3–4 which upon extraction and evaporation yields 4-(17'alpha-estradiol-4'-hydrazo) benzoic acid. Thin layer partition chromatography yields the desired purified fluorescent 4-aminoestradiol and hydrazoestradiol benzoic acid derivatives.

EXAMPLE 5

PREPARATION OF 4-(17'BETA-ESTRADIOL-4'-AZO)BENZOYL KEYHOLE LIMPET HEMOCYANIN (KLH)

0.1 Molar 1-cyclohexyl-3-(2-morpholinoethyl) carbodiimide metho-p-toluene sulfonate (100 mg) in a 1% saline solution is added to purified crystalline azobenzoyl 4-(17'beta-estradiol-4'-azo)benzoic acid (25 mg). The desired intermediate 0-1,3-dicyclohexyl-2-[4-(3',17'beta-dihydroxestra-1',3',5'-trienyl-4'-azo)benzoyl]pseudourea is thereby produced.

KLH is added to the foregoing mixture. The mixture is stirred unitl the intermediate azopseudourea has coupled to the KLH and is dialyzed for 2–3 days at 3° C in 0.5M sodium carbonate, pH 8.2 until color no longer appears in dialysis solution. A final dialysis is performed against 0.9% NaCl for 24 hours. The preceding steps removed unreacted steroid and derivative molecules. Insoluble protein is removed by centrifugation. Protein determination is made on the colored supernatant containing the 4-(17'beta-estradiol-4'-azo)benzoyl KLH conjugate. This supernatant is lyophilized after dialysis against triple distilled water.

When Example 5 is repeated with the exception that a like amount of immune gamma globulin or bovine serum albumin is substituted for KLH as the protein, 4-(17'beta-estradiol-4'-azo)benzoyl immune gamma globulin and 4-(17'beta-estradiol-4'-azo)benzoyl bovine serum albumin are respectively produced. The reactions proceed through the corresponding intermediate protein -pseudoureas (VI).

EXAMPLE 6

PREPARATION OF 4-(ESTRIOL-4'-AZO) BENZOYL KEYHOLE LIMPET HEMOCYANIN 0.1 Molar 1-cyclohexyl-3-(2-morpholinoethyl)carbodiimide metho-p-toluene sulfonate (100 mg) in a 1% saline solution is added to purified crystalline 4-(estriol-4'-azo)benzoic acid (25 mg). The desired intermediate 0-1,3,-dicyclohexyl-2-[4-3',16'alpha,17'beta-trihydroxyestra1',3',5',-trienylazo)benzoyl] pseudourea is thereby produced. KLH (250 mg) is added to the foregoing mixture. The mixture is stirred until the intermediate azopseudourea has coupled to the KLH and is dialyzed for 2–3 days at 3° C in 0.5M sodium carbonate, pH 8.2 until color no longer appears in dialysis solution. A final dialysis is performed against 0.9% NaCl for 24 hours. The preceding steps remove unreacted steroid and derivative molecules. Insoluble protein is removed by centrifugation. Protein determination is made on the colored supernatant containing the 4-(estriol-4'-azo) benzoyl KLH conjugate. This supernatant is lyophilized after dialysis against triple distilled water.

When Example 6 is repeated with the exception that a like amount of immune gamma globulin or bovine serum albumin is substituted for KLH as the protein, azobenzoyl estriol immune gamma globulin and azobenzoyl estriol bovine serum albumin are respectively produced. The reactions proceed through the corresponding intermediate protein-pseudoureas (VI).

EXAMPLE 7

PREPARATION OF 4-(ESTRONE-4'-AZO) BENZOYL KEYHOLE LIMPET HEMOCYANIN 0.1 Molar 1-cyclohexyl-3-(2-morpholineothyl)carbodiimide metho-p-toluene sulfonate (100 mg) in a 1% saline solution is added to purified crystalline 4-(estrone-4'-azo)benzoic acid (25 mg). The desired intermediate 0-1, 3-dicyclohexyl-2-[4-(3'-hydroxy-17'-oxoestra-1',3',5'-trienylazo)benzoyl] pseudourea is thereby produced. KLH (250 mg) is added to the foregoing mixture. The mixture is stirred until the intermediate azopseudourea has coupled to the KLH and is dialyzed for 2–3 days at 3° C in 0.5M soidum carbonate, pH 8.2 until color no longer appears in dialysis solution. A final dialysis is performed against 0.9% NaCl for 24 hours. The preceding steps remove unreacted steriod and derivative molecules. Insoluble protein is removed by centrifugation. Protein determination is made on the colored supernatant containing the 4-estrone-4'-azo)-benzoyl KLH conjugate. The supernatant is lyophilized after dialysis against triple distilled water.

When Example 7 is repeated with the exception that a like amount of immune gamma globulin or bovine serum albumin is substituted for KLH as the protein, 4-(estrone-4-azo)benzoyl immune gamma globulin and 4-(estrone-4'-azo)benzoyl bovine serum albumin are respectively produced. The reactions proceed through the corresponding protein-pseudoureas (VI).

EXAMPLE 8

PREPARATION OF 4-(17'ALPHA-ESTRADIOL-4'-AZO) KEYHOLE LIMPET HEMOCYANIN 0.1 Molar 1-cyclohexyl-3-(2-morpholinoethyl)carbodimide metho-p-toluene sulfonate (100 mg) in a 1% saline solution is added to purified crystalline 4-(17'alphaestradiol-4'-azo)benzoic acid (25mg). The desired intermediate 0,1,3-dicyclohexyl-2-[4-(3',17'alpha-dihydroxestra-1',3',5'-trienylazo)benzoyl]pseudourea is thereby produced. KLH is added to the foregoing mixture. The mixture is stirred until the intermediate azopseudourea has coupled to the KLH and is dialyzed for 2–3 days at 3° C. in 0.5M sodium carbonate, pH 8.2 until color no longer appears in dialysis solution. A final dialysis is performed against 0.9% NaCl for 24 hours. The preceding steps remove unreacted steroid and derivative molecules. Insoluble protein is removed by centrifugation. Protein determination is made on the colored supernatant containing 4-(17'alpha-estradiol-4'-azo)KLH conjugate. This supernant is lyophilized after dialysis against triple distilled water.

When Example 8 is repeated with the exception that a like amount of immune gamma globulin or bovine serum albumin is substituted for KLH as the protein, 4-17'alpha-estradiol-4'-azo) immune gamma globulin and 4-(17'alphaestradiol-4'-azo)bovine serum albumin are respectively produced. The reactions proceed through the corresponding intermedite protein-pseudoureas (VI).

Other haptens or even intact protein antigens (containing tyrosine, tryptophan, or histidine) can be employed in place of the steroids (I) in Reaction Sequence I of the instant invention, provided the hapten or antigen contains an aromatic moiety (e.g. catecholamines) or heterocyclic moiety, preferably completely or partially unsaturated, of 5-6 ring atoms (e.g. histidine or tryptophan). Exemplary of the aromatic moiety is the following structure:

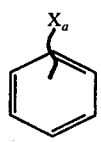

wherein X and a are as previously defined. Exemplary haptens or antigens are: the catecholamines, 1-(3,4-dihydroxyphenyl)2-methylamino)ethanol; beta-(p-hydroxyphenyl)alanine; beta(3,4-dihydroxyphenyl)-alpha-alanine; 3,4-dihydroxyphenethylamine; 2-amino-1-(3,4-dihydroxyphenyl)ethanol; indoleamines, such as beta-3-indolylalanine; 5-hydroxytryptophan; or 5-hydroxytryptamine. In addition psychomimetic agents, e.g. mescaline, morphine, tetrahydrocannabinol, demerol, the amphetamines, the tricyclic antidepressants such as the dibenzocycloheptenes (e.g. amitriptyline, nortriptyline), imipramine, the phenothiazenes, the benzoquinolizines, reserpine, the diazepoxides (e.g. librium, valium), diethylstilbestrol, insulin, angiotensin, thyroxin, aldosterone, growth hormone, lactogen, (bovine) insulin, follicle stimulating hormone, lutenizing hormone, human chorionic gonadotropin, pitocin, adrenocorticotropin, thyrotropin, or any polypeptide containing the tryptophan, histidine or tyrosine residues (e.g. see Atlas of Protein Sequence and Structure by M.O. Dayhoff, National Biomedical Research Foundation, Silver Springs, Md., 1968, for example pages 235–272, and Vol. 4, 1969, pages D67-D172) can be employed. Furthermore, conjugaged Δ,4,5-steroids can be employed wherein the A ring has the following structure:

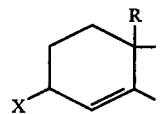

wherein R is H, or lower-alkyl and X is keto, —OH, or amine (as defined above). Exemplary is testosterone. Thus A in the following Reaction Sequence II can be another hapten, intact polypeptide, or Δ,4,5-steroid, each as defined above, containing an aromatic group, or heterocyclic nucleus with aromatic character, substituted with an ortho, para or meta directing group (as previously defined for X) which permits a diazonium ion to bind to A by coupling directly to an atom of said aromatic group. R', R''', R'''' and the protein are as previously defined.

Reaction Sequence II

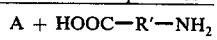

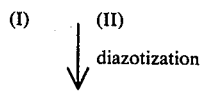

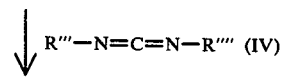

-continued
Reaction Sequence II

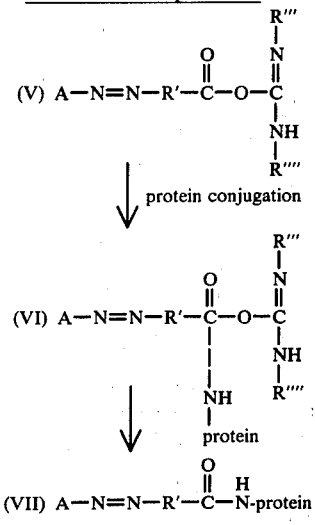

The procedure in the foregoing sequence can be that employed in Reaction Sequence I.

The novel antibodies raised in animals upon immunization by administration of the novel antigenic substances of this invention form a novel embodiment thereof. The antibody produced by administration of an antibody producing dose of the foregoing steroid-protein antigenic substance, catecholamine-protein antigenic substance, and polypeptide hapten-protein or antigenic protein substance alone, in their substantially pure form is recovered from the crude antisera thereby raised in animals as follows:

The crude antisera is exposed to immunoadsorbants. These adsorbants are set forth in Kabat (supra) and Weliky et al; Immunochemistry 1,219 (1964). They generally comprise cellulose derivatives or aryl-NH$_2$ substituted glass (such as disclosed hereafter), with available amino or carboxylic groups forming a solid matrix to which the antigenic compounds of this invention are conjugated as described for conjugation to proteins (supra). When the crude antisera is exposed to these modified sorbants the desired specific antibody for the unique hapten is retained thereon. The remaining sera constituents or antibodies are passed through and not retained and can, if desired, be recovered, for example, by centrifugation or passage through DEAESephadex. Antibody bound to the matrix is removed by a mixture of 0.5–1.5N, preferably 1N, acetic acid (or HCl) and 2–4M, preferably 3M urea, pH 3.4–3.6. Recovery ranges from 90–98% of the theroretical total. Immunological activity is retained. (This mixture used to elute antibody in an underivatized state from a hydrophobic hapten, is novel and can also be employed to extract free and protein-bound haptens from serum (proteins) by treatment with the foregoing mixture and suitable adjustment of pH to effect extraction.) After immediate neutralization with 0.1N NaOH, the antibodies are isolated and these antibodies are precisely specific for the appropriate derivative which had been attached to the matrix. This can be utilized to recover specific antibodies from the crude sera or alternatively can be utilized to recover unwanted cross-reacting antibodies.

Exemplary of the new antibodies of this invention are those having the following characteristics:

Estradiol Antibody:

It is generated by administering an antibody-producing amount of 4-(17'beta-estradiol-4'-azo) benzoyl KLH (or KLH replaced by another carrier such as IgG or BSA), and identified by the following characteristics showing specificity for estradiol:

1. Double diffusion in agar or immunoelectrophoresis tests. These are standard tests. Double diffusion in agar is a test in which 1.0% agar (0.6–3 ml) is poured onto a piece of glass. Small wells are produced in the agar (after solidification) by a template. Peripheral wells are equidistant from the center well. A variety of hapten-protein conjugates are placed in aqueous solution in each of the outer wells and thereby tested against a sample of antibody placed in the center well. The slide containing the solidified agar and wells containing solutions of antigen conjugate and antibodies are allowed to incubate in a moist atmosphere for 24 hours on average. A precipitin line, or arc, is noted to appear anywhere from 3 hours to 48 hours, if the antibody is specific as shown by reaction with the hapten-protein conjugate. Immunoelectrophoresis is performed in the following fashion: After pouring 3 ml of agar on a standard microscopic slide and permitting the agar to harden, one or more wells, are stamped by a template toward one end of the slide, approximately equidistant from one or more horizontal troughs, traced by the template between each of the wells. The source is permitted to deliver approximately 6 milliamps per slide tested and electrophoresis is carried on for 45 minutes to an hour. At this time the current is turned off, the agar is removed from the precut trough, antiserum placed in the trough and the slide put in a moist chamber to incubate for 4 hours to 48 hours. When there is antibody specific for the hapten-protein conjugate the precipitin arc appears. The arc generally appears almost under the well and moves slightly toward the negative electrode. When testing 4-(17'beta-estradiol-4'-azo)benzoyl IgG conjugate against 4-(17'beta-estradiol-4'-azo)benzoyl KLH antiserum, an estradiol-specific precipitin line appears, the two different proteins do not cross-react.

2. Quantitative precipitin tests. To each one of a series of test tubes is added 0.5 ml of a standard antibody solution, either serum or buffered IgG in solution, approximately 2 to 10 milligrams per ml. To each of the tubes is added 0.25 to 0.5 ml of hapten in concentrations ranging from 1 to 200 micrograms per ml. The tubes are permitted to incubate at 37° for 2 hours and thereafter for 2 days at 4° C. At the end of this time the tubes are centrifuged at 6000 r.p.m., washed 4 times with buffered saline, then dissolved in sodium hydroxide and a Lowry method protein determination is performed. After subtracting the known amount of protein conjugate which was added, the total antibody protein precipitated by the known conjugate is determined by subtraction. Purified estradiol antibody does not cross-react with estrone and only slightly with estriol. 300–1200 μg/ml antibody protein (estradiol-specific) is recovered after short term immunization (6 weeks).

3. Hapten inhibition tests. After permitting the antibody to pre-incubate with 4-(4'-azoestradiol) benzoic acid, 4-(4'-azoestrone)benzoic acid, or 4-(4'-azoestriol)-benzoic acid, not coupled to proteins, the antibody is then permitted to interact with known concentrations of hapten-protein conjugate, as in the preceding test and the preceding test then carried out as described above. Hapten inhibition weakens, or blocks,* antibody so that the more hapten there is permitted to interact preliminarily with antibody, the less precipitation results upon subsequent interaction with steroid-protein conjugate. The heterologous haptens do not inhibit the estradiol antibody quantitatively. If a hapten does not inhibit an antibody solution, the antibody is not specific for that hapten. A quantity of 2–10 ug/ml 4-(4'-azoestradiol)-benzoic acid inhibits (100%) 1 ml homologous hapten-specific antiserum (i.e. estradiol antibody).

* Forms a soluble complex.

4. Fluorescence quenching of antibody at emission, 350mm (as described hereafter). The average estradiol specific association constant is Ko-$10^7$.

5. Fluorescence enhancement of hydrazo and amino estradiol at emission 420mm (as described hereafter) The average estradiol specific association constant is Ko = $10^7$.

Estriol Antibody:

It is generated by administering an antibody-producing amount of 4-(estriol-4'-azo)benzoyl KLH (or other protein such as IgG or BSA) and identified by the following characteristics showing specificity for estriol in accordance with the tests previously described for estradiol antibody.

1. Double diffusion in agar or immunoelectrophoresis tests. When testing 4-(estriol-4'-azo)benzoyl IgG conjugate against 4-(estriol:4'-azo)benzoyl KLH antiserum, an estriol-specific precipitin line appears.

2. Quantitative precipitin tests. 300–1200 ug/ml antibody protein (estriol-specific) which does not cross-react with related estratrienes is recovered after short-term immunization (4–6 weeks).

3. Hapten inhibition tests. 1-5 ug/ml 4-(estriol-4'-azo)benzoic acid inhibits 1 ml antibody (100%).

4. Fluorescence quenching of antibody (discussed more fully hereafter). The average estriol specific association constant is Ko = $10^7$.

5. Fluorescence enhancement of hydrazo and amino estriol (discussed more fully hereafter). The average estriol specific association constant is Ko = $10^7$.

As discussed above, the novel antigenic substances of this invention produce antibodies specific for the test compound corresponding to the hapten. Thus immunologic assays employing these antibodies are reliable and accurate. An embodiment of this invention is novel clinical assays for homologous, naturally occurring metabolites in body fluids. Such assays employ novel fluorescent compounds of the following structures which also constitute an embodiment of this invention.

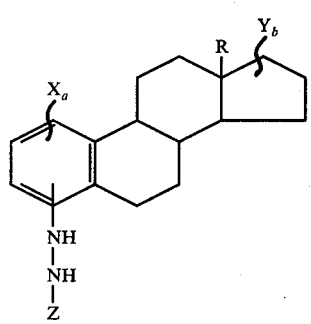

(I)

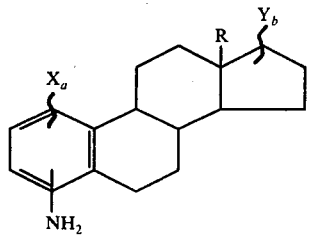

(II)

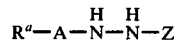

(III)

(IV)

wherein A, X, Y, R, $a$, and $b$ are as defined before. $R^a$ is hydrogen, alkyl, alkenyl, or alkynyl, preferably containing from about 1 to about 10 carbons. When unsaturated, $R^a$ can be mono- or poly-unsaturated, although it is preferred that $R^a$ contain no more than 1 or 2 unsaturated linkages which preferably are in a conjugated configuration. Furthermore $R^a$ can be a mono- or polycyclic residue which, when fused to A at adjacent ring atoms thereof, forms a fused ring moiety illustrated by the following: naphthyl, anthryl, phenanthryl, indyl, isoindyl and the like. $R^a$ can also be a straight or branched chain, saturated or unsaturated, aliphatic group, preferably containing from about 1 to about 10 carbon atoms. Exemplary are methyl, ethyl, propyl, isopropyl, butyl, isobutyl, tertiary butyl, i.e. lower-alkyl; ethenyl and the corresponding mono- or di-unsaturated derivatives of the foregoing lower-alkyls; alkynyl such as ethynyl, propynyl and the like; cycloaliphatic preferably containing from about 4 to about 10 carbons such as cyclobutyl, cyclopentyl, cyclohexyl cyclooctyl, and substituted derivatives thereof preferably wherein the substituents are lower-alkyl, aryl such as phenyl, naphthyl and the like; aryl groups containing from about 6 to about 10 carbons; cycloolefinic groups containing from about 5 to about 10 carbons and preferably containing mono unsaturation such as cyclopentenyl, cyclohexenyl, cycloheptenyl, cyclooctenyl, and the lower-alkyl substituted derivatives thereof, as well as polyunsaturated cycloolefinic groups such as cyclopentadienyl or 1,3,5-cyclooctotrienyl.

Z is any moiety capable of sustaining a diazonium ion, (e.g. see P.H. Hermans (Elsevier) e.g. pp. 279–290*), such as an unsubstituted aryl, preferably phenyl or naphthyl, containing from about 6 to about 14 carbons; or a substituted aryl containing 1-3 groups which do not interfere with the formation of a diazonium ion, (i.e. sustained by the amine moiety, —R'NH$_2$), preferably those groups selected from the following: amino, nitro, halo, (i.e. chloro, bromo, fluoro, iodo), HSO$_3$, carboxyl, or a fused ring moiety such as naphthyl or terphenyl. Exemplary of compounds from which Z is derived are: p-aminobenzoic acid; benzene diazonium halide, preferably chloride, (meta, or di or tri substituted with NH$_2$, NO$_2$, halo COOH); any aryl amine (which can be additionally substituted in the 1,2, or 3 sites of the aryl ring with such as NO$_2$, halo, COOH, or lower-alkyl); any diazonium salt wherein the diazonium group is attached to an aryl or heterocyclic group with aromatic character, e.g. piperidine, pyrazole, triazole, benzyrene; metal chelates, e.g. (tris-(acetyl acetonate chromium); hyponitrite ester, e.g. RO—N=N—OR (wherein R is lower-alkyl); thio analouges of azobenzene e.g. RN=S=NR, where R is lower-alkyl.

*First English Edition Amsterdam (1954). Also see P.A.S. Smith, The Chemistry of Open Chain Nitrogen Compounds, Vol. 1, pp. 100-105 (1965) W. A. Benjamin, N.Y.

These hydrazo or corresponding amino derivatives are produced by mild reduction of the corresponding azo compounds and are highly fluorescent. The resulting hydrazo and amino compounds by virtue of their absorbence and excitation peaks, which overlap the emission spectrum of specific antibody, exhibit quenching (as do the corresponding azo compounds) of fluorescence emission of the novel antibodies of this invention. These antibodies also enhance the natural fluorescence of the hydrazo derivatives upon specific binding because of the overlap of the emission of the antibody and excitation of the hapten derivative. Thus the antibodies and the novel hydrazo derivatives are ideally compatible for use, employing either quenching or enhancement, in a simple, straightforward spectrophotofluorometric quantitation.

In producing the novel fluorescent compounds of this invention by reduction of the corresponding azo intermediates, the reaction proceeds according to the following reaction sequence III, wherein X, Y, R, A, $R^a$, Z, a and b are as previously defined. From the reaction sequence it can be seen that reduction of the azo compound (I) and (II) produces a mixture of hydrazo and amino derivatives (III) and (IV) or (V) and (VI) respectively. Ratios of hydrazo to amino derivatives in the mixture depend on the substituents on the starting materials, the reducing agent and kinetics. For example, in the case of reduction of 4-(4'-azostriol) benzoic acid using sodium borohydride, a ratio of 1:4 hydrazo to amino derivatives is produced. The amino steroid derivatives (IV) and (VI) are produced in excess. Separation of these derivatives is achieved using conventional chromatography and extraction techniques.

In carrying out the reduction of the azo derivative in accordance with reaction Sequence III when an alkali metal borohydride is employed, a large excess of the borohydride (preferably comprising a mixture of tetrahydrofuran, methanol and water) is added to the azo derivative. Additionally, water can be added to effect the reaction. As a practical matter, water and borohydride can be added incrementally to control the reaction until completion as evidenced by loss of color of the reaction mixture. As a rule of thumb, an 8 molar excess or greater of reducing agent is employed.

REACTION SEQUENCE III

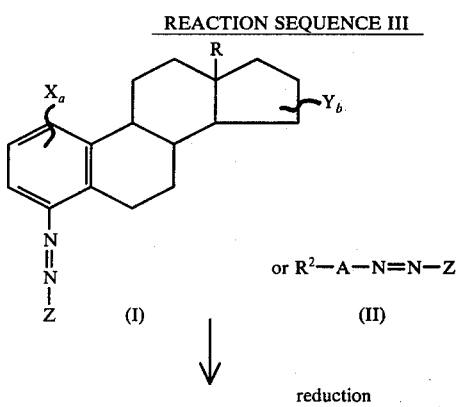

or $R^2-A-N=N-Z$ (I)     (II)

↓ reduction

-continued
REACTION SEQUENCE III

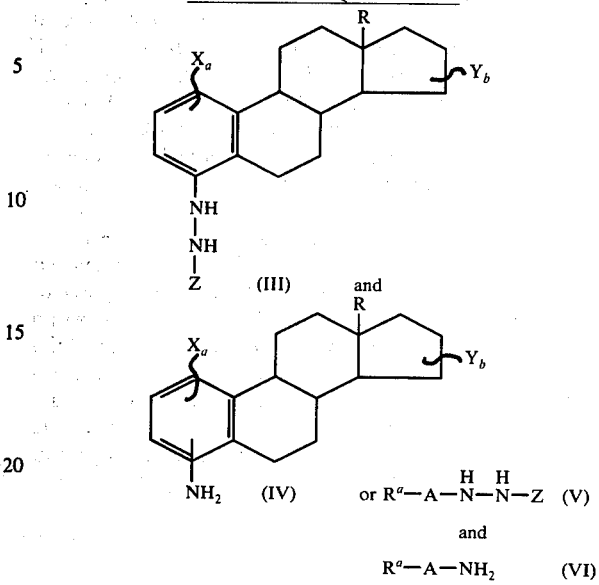

or $R^a-A-\overset{H}{N}-\overset{H}{N}-Z$ (V)

and $R^a-A-NH_2$ (VI)

EXAMPLE 9

A. PREPARATION OF 4-(INSULIN-AZO)BENZOIC ACID

300 Milligrams of p-aminobenzoic acid is dissolved and stirred in 10 ml of 1 N HCl in a 20 ml beaker surrounded by ice. The temperature is maintained below 5° C. 150 Milligrams of sodium nitrate is dissolved in 5 ml of water and added under the surface of the p-aminobenzoic acid solution slowly. The temperature is maintained below 5° C. and pH is maintained at 1. The reaction mixture is stirred for 20 minutes. Excess sodium nitrate is removed by treatment with 10 milligrams of sulfamic acid after 20 minutes. Bovine insulin (50 mg) is dissolved in 1/10 molar phosphate buffer, pH 11. The diazotized p-amino benzoic acid is added to this solution dropwise. The pH is maintained at 11 with 2 N sodium hydroxide and the mixture is stirred for 10 minutes. Then the 4-(azo-insulin)benzoic acid is stirred against repeated charges of water. Oxidation is prevented by final dialysis at pH 5.5 (acetate or $H_2O$) and lyophilization in vacuo.

B. PREPARATION OF 4-(HYDRAZO INSULIN)BENZOIC ACID AND AMINO INSULIN

A one ml aliqot containing approximately 1 mg of the diazotized insulin of step A is reduced with sodium borohydride (8 molar excess) until only a slight color remains. The solution containing amino insulin and 4-(hydrazo insulin) benzoic acid derivative (9:1 amino to hydrazo) (of which an average of 2.5 tyrosyl and 1.5 histadyl residues of the insulin chains are substituted) is neutralized with 1 N acetic acid. It is isolated as described above.

An aliquot of 4-(hydrazoinsulin) benzoic acid produced in step B and purified by chromatography (1 mg) is stirred with 14 mgs of soluble cyclohexylcarbodiimide. The insulin derivative is condensed with .4 mg of normal insulin. The resulting conjugate consists of bovine serum insulin and reduced fluorescent A and B chains of insulin, i.e. 4-(hydrazoinsulin)benzoic acid (as defined in step B). Molar ratios of reduced chains bound to insulin (2:1) are calculated after ascertaining the amount of normal hydrazo and amino derivatives of tyrosine and histidine by amino acid analysis for which known amino acids (for insulin) and their amino and hydrazo derivatives are used as reference standards.

Reduction by sodium hydrosulfite (6 molar excess) in place of sodium borohydride in Example 9 produces in excess of 90% hydrazoinsulin derivative. Oxidation is prevented by acidification, treatment with an anti-oxidant (2,6-di-tert-butyl p-cresol) and lyophilization.

4-(Hydrazophenol)benzoic acid (2' and 4' isomers and o and p-aminophenol are similarily prepared by diazotizing para-aminobenzoic acid followed by reduction with an excess of sodium borohydride. Separation of the resulting aminophenols (90%) and 4-(hydrazophenol)-benzoic acids (10%) (ratios are reversed by sodium hydrosulfite) is effected by extraction into ethyl acetate followed by removal of the remaining hydrazophenol from the aqueous phase (ph 2) by an organic solvent, and partition chromatography.

4-(Hydrazoepinephrine)benzoic acid and aminoepinephrine are prepared following the procedure of Example 9 with the exception that epinephrine is employed as a starting material in preparation rather than bovine insulin. Oxidation is prevented by performing the reaction under $N_2$, using excess sodium borohydride or hydrosulfite, acidification, and use of an antioxidant as described above and lyophilization in vacuo.

EXAMPLE 10

PREPARATION OF PHENOLAZO GLASS DERIVATIVES

Approximately 100 milligrams of amino glass beads* are stirred in 1 N HCl (5 ml) cooled to 5° C by an ice bath. Approximately 150 milligrams of sodium nitrite are dissolved in water (5 ml) and added dropwise under the surface of the solution containing the glass derivative. The phenol (150 mgs) is added dropwise over a five minute period. The reaction mixture is stirred 20 minutes, at a temperature maintained below 5° C. After washing with 3 changes of distilled water the phenolazo glass beads (o and p derivatives) are placed in 10 ml of fresh distilled water. Several drops of 1M acetic acid and 100 milligrams of sodium borohydride are added successively. After neutralization with acetic acid the supernatant is separated from the beads by centrifugation. The beads are washed with 3 changes of distilled water. Under a UV light source (Zeiss mercury burner) both the supernatant, containing the soluble o and p aminophenols and the insoluble phenol hydrazo glass (o and p derivatives) are highly fluorescent. The former appears light blue, the latter bright red.

* Porous, 96% silica glass, 40 A ± 20 A diameter pore size (Corning Glass Works, Corning, N.Y.) in a toluene solution gamma-aminopropyl triethoxy silane, is refluxed. This mixture is reacted with p-nitrobenzoic acid and reduced with tetrachloromethane to produce the desired aryl amino glass. (See Weetall, Biochem. J. (1970) 117,257-261)

Amino glass and other insoluble matrices produce in like fashion from the homologous parent azo compound, soluble amino insulin, amino epinephrine, amino estradiol, amino estriol, amino estrone and their corresponding insoluble hydrazo derivatives. In each instance the insoluble hydrazo derivative is fluorescent as is the supernatant containing the amino derivative.

Soluble and insoluble azo, hydrazo and amino derivatives are utilized in unique assays employing fluorescence enhancement or quenching as well as radioimmune techniques to quantitate concentrations of underivatized homologues.

Utilizing the same molar ratios as described in Examples 9 and 10 there are prepared the corresponding soluble amino, hydrazo and insoluble hydrazo-glass derivative of angiotensin thyrotropic releasing factor (TRF) (a tripeptide containing histidine), lactogen, pitocin, and growth hormone.

Amino glass and its preparation is well known, for example, see J. Biochem. 117: 257–61 (1970); Biochem. Biophys. Acta, 185:464 (1969); Science 166:615(1969); Nature 223:959(1969). Thus the porous glass can be refluxed in solution of aminopropyltriethoxysilane in toluene, or the isothiocyanate derivative can be prepared by refluxing alkyl amine glass overnight in a 10% solution of thiophosgene in chloroform. The glass is then washed in chloroform, dried and coupled to hapten in carbonate buffer. Aryl - amino glass derivatives can also be prepared by reacting alkylaminosilane glass with p-nitrobenzoyl chloride in chloroform containing 5% triethylamine. The nitro groups are reduced with sodium dithionite ($N_2S_2O_4$). Tetrachloromethane serves the same purpose. The arylamino glass is then diazotized and coupled to the hapten (or antigen) as described above.

Thus an embodiment of this invention comprises hapten azo-glass or conjugated hapten-protein azo-glass and corresponding fluorescent hydrazo and amino derivatives of the following structures (in addition to glass other insoluble matrices can be employed, hence the designation M in the following structure):

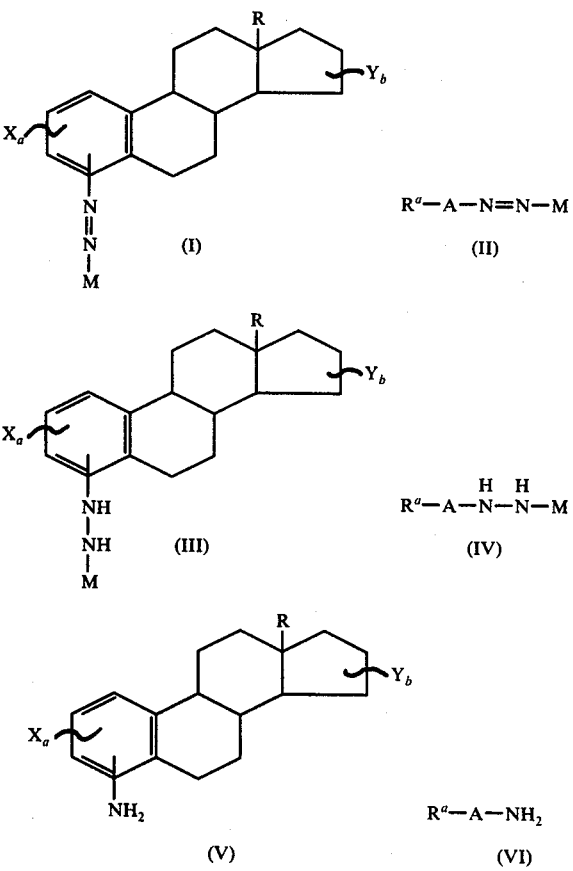

wherein R, X, Y, A, a and b are as previously defined and M is an insoluble inorganic matrix containing a reactive NH₂ (e.g. amino glass derivative as defined herein) or an insoluble organic matrix containing a reactive NH₂, OH or COOH (e.g. Sephadex or cellulose derivatives). See Weliky et al, Immunochemistry, 1, 219(1964). *

* Any insoluble solid material can be employed which does not interfere with the hereinafter described immune assays by attracting the compound under assay non-specifically. See also U.S. Pat. No. 3,519,538, issued July 7, 1970), for example,Column 3, lines 44 et seq.

The compounds of the foregoing structures I-IV are produced, for example, by utilizing the insoluble solid matrix derivative for covalently coupling directly to the hapten or antigen through the ring moiety of the hapten or antigen, as by diazotization in accordance with procedures of this invention. The insoluble solid matrix derivatives used for coupling are well known compounds as previously described in connection with the definition of M. The coupled azo product (I and II) is then reduced under mild conditions to produce the corresponding hydrazo (III and IV) and amino (V and VI) derivatives.

Coupling of hapten or antigen to a solid matrix, such as amino glass, presents the opportunity for an easy separation of the soluble amino derivatives (V and VI) from the insoluble hydrazo derivatives (III and IV). In such cases separation is accomplished by simple washing and filtration or centrifugation.

The following Example 11 further illustrates the preparation of the novel antibodies of this invention. As previously discussed, these antibodies are useful in immunochemical assays discussed hereinafter because of their specificity and fluorescence emission characteristics.

EXAMPLE 11

A total dose of 30-100 mg per animal of the antigen is administered (pure form) as a 1% aqueous solution (by weight of antigen) in normal saline to a New Zealand white rabbit, weighing 5 kg (males used to prepare antibodies to estrogens, otherwise sex immaterial). The antigen is administered every other day intravenously for one week (i.e. three times a week). Two weeks later an equal total dose of the antigen emulsified in an equal volume of complete Freunds adjuvant is administered subcutaneously (once only). Three weeks later blood is drawn (50 ml). Serum is separated by centrifugation. It is passed through a solid matrix, diethylaminoethylcellulose-Sephadex A50 (Pharmacia, Uppsala, Sweden) and IgG is isolated. Antibody is purified by hapten-coupled-p-aminobenzyl cellulose (e.g. estradiol-p-aminobenzyl cellulose). Specific antibody bound to the cellulose solid matrix is eluted (after repeated washing with water) by a mixture of 1 M acetic acid and 3 M freshly prepared deionized urea pH 3.2. Table I set forth specific antibodies of this invention, and antigens used for their preparation in accordance with the foregoing procedure.

TABLE I

| Antigen | Dose | Antibody Specific For |
| --- | --- | --- |
| estradiolazobenzoyl-KLH of Example 5 | 30 mg | estradiol (17β) |
| estriolazobenzoyl-KLH of Example 6 | 30 mg | estriol |
| estroneazobenzoyl-KLH of Example 7 | 20 mg | estrone |
| insulinazobenzoic acid of Example 9 | 50 mg | insulin |
| Tetrahydrocannabinol azobenzoyl-KLH* 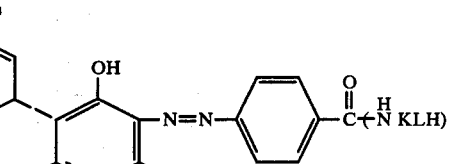 | 20 mg | tetrahydrocannabinol |
| (L-Pyroglutamyl-L-histidyl-L prolineamide) azobenzoyl-KLH* 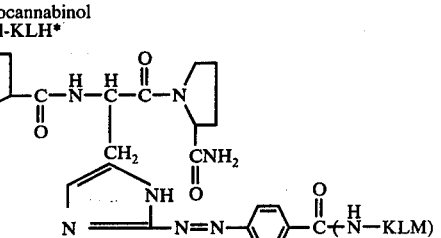 | 10 mg | thyrotropic releasing hormone |

*Prepared in accordance with the method of Example 5 by substituting equimolar quantity of THC or TRH for the estradiol.

The foregoing novel conjugates, antibodies and fluorescent derivatives of this invention are especially adapted for use in the several embodiments of the novel assay methods of this invention.

One of these embodiments comprises an immunofluorescent method of assaying quantitatively for compounds of structures (I), and (I) herein, which comprises producing a mixture, suitable for fluorometric assay, or (1) a sample to be analyzed, generally from body fluid (although any sample source can be employed) and containing the compound under assay, (2) a known quantity of an antibody which is immunologically specific for the compound to be assayed, and (3) a known quantity of a hapten or antigen derivative, possessing an absorbance spectrum (345± 10 nanometers) corresponding to the emission spectrum of the antibody, and which is homologous to said assay compound (that is, sharing immunochemical specificity) so as to bind with said antibody competitively; and analyzing said mixture for antibody fluorescence quenching.

Exemplary of the compounds which can be assayed are the following:

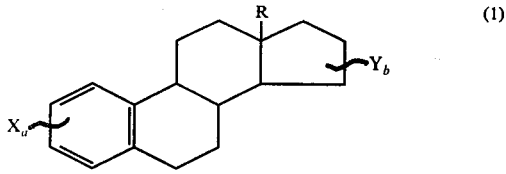

wherein X, Y, R, $a$ and $b$ are as previously defined;

(2) psychomimetric agents as exemplified by the amphetamines, meperidine, mesealine or tetrahydrocannabinol, i.e. the active constituent of marihuana (hashish);

(3) a catecholamine, as defined before;

(4) a polypeptide, as previously defined;

(5) diethylstibestrol;

(6) a $\alpha$, 4,5-steroid as defined before; and (7) chlortetracycline, tetracycline and chloramphenicol.

The hapten or antigenic derivatives which can be employed to quench the fluorescence of the antibody are typified by the structures III, V, VI and VII, VII, IX and X, III, V, VI and VII; I-III; I-V, and I-V herein.

The assay for fluorescence quenching is as follows:

A. Establishment of Standard Curve for Sample to be Assayed

One ml of antibody ($1 \times 10^{-10}$ moles per ml) is added to each of a series of 30 test tubes. To each one of the tubes is also added 1 ml containing concentrations of hapten or antigen derivative starting with the first tube with a concentration of $1 \times 10^{-10}$ moles per ml of hapten or antigen up to the last tube which contains $30 \times 10^{-10}$ moles per ml of hapten or antigen. Then an optional mixture, (e.g. $1 \times 10^{-10}$ M/ml) antibody and $6 \times 10^{-10}$ M/ml hapten, or antigen derivative, are interacted with an ml of competing underivatized hapten, i.e. assay compound, in increasing concentrations (e.g. $1-10 \times 10^{-10}$ M/ml). This mixture is allowed to incubate for 10 minutes to 12 hours at ambient temperature and is then read in a spectrophotofluorometer for fluorescence quenching. Standard tubes contain an equivalent concentration, either of antibody or of hapten diluted in buffer, in the same concentration present when antibody and hapten are mixed together. Excitation is set at 280 nanometers and emission read at 350 nanometers. The sum of the fluorescence emission for hapten alone at a set concentration and for antibody alone at a set concentration are added. This sum is equal to 100% fluorescence. The actual fluorescence intensity observed upon interaction of antibody and derivatized hapten will read less than 100% because of quenching as a result of the binding of the derivative to the antibody. With increasing concentration of derivatized hapten the observed fluorescence diminishes until hapten-antibody interaction (or binding) is completed. The difference between the fluorescence of the completely interacted hapten-antibody mixture and the sum of the fluorescence of hapten and antibody alone constitutes the percent of quenching. The percent of quenching is proportional to the concentration of hapten derivative.

In assaying a sample of underivatized hapten or antigen, an optimal standard ratio of derivatized hapten and antibody (e.g. 5–10:1) is selected for use in testing the underivatized sample. The latter (e.g. estradiol) in increasing concentrations per ml, competes with the hapten or antigen derivative for binding with a given amount of antibody and will inhibit the quenching phenomenon, permitting fluorescence by antibody bound thereto. The percent of increase in antibody fluorescence caused by binding with underivatized hapten or antigen sample is directly proportional to the concentration of the underivatized hapten or antigen. The relationship is rendered linear. The more competing unaltered hapten or antigen present in the solution, the less fluorescence quenching is caused by the derivatized hapten or antigen. Hence a standard curve can be drawn for an unknown solution.

B. Assay for Underivatized Hapten or Antigen

The solution containing the sample (i.e. underivatized hapten or antigen as previously described) can be a neutral aqueous solution or body fluid (e.g. serum, urine, amniotic fluid, or tissue extract).

To establish the concentration of the unknown in the body fluid the fluorescence intensity of the sample mixture (containing antibody, derivatized hapten or antigen, and the unknown) is compared with the aforementioned standard curve. The control for such assay is body fluid known to contain no underivatized hapten or antigen.

Thus in carrying out the assay a sample of body fluid is obtained and is added (after solids are removed by centrifugation) in dilution to a standard mixture of antibody and derivatized homologous hapten or antigen, the latter being present in a molar excess (preferably ranging from 5–10:1). The resulting solution is allowed to incubate at ambient temperature for about 15 minutes to 12 hours. Thereafter the fluorescence of the resulting mixture is determined, generally by a spectrophotofluorometer. The reading from this instrument (at 350 mm emission) is compared with the standard curve for the compound under assay and translated to the concentration of sample compound present (ng/ml).

Example 12 illustrates the fluorescence quenching assay of this invention for quantitation of a variety of underivatized haptens or antigens.

EXAMPLE 12

An aliquot (1–10 ml) of blood is obtained from a patient. Solids are removed by centrifugation. The clear serum is added to a standard mixture of antibody and derivatized homologous hapten or antigen (molar ratio 1:6 antibody to hapten). The resulting mixture is incubated at ambient temperature for about 15 minutes. Thereafter the fluoresecence of the resulting mixture is measured in an Aminco-Bowman spectrophotofluorometer (correction being made for contribution of buffer and non-specific serum contents as established by the controls). The measured fluorescence intensity is compared with the standard curve for the compound under assay and thereby translated into the concentration of sample compound present.

The following Table 2 sets forth the constituents used in each assay for the indicated sample compound in accordance with the method of this example.

TABLE 2

| Sample to be Assayed | Quenching Hapten or Antigen derivatives | Fluorescent Antibody |
|---|---|---|
| estradiol (17β) | estradiol azobenzoic acid of Example 1 | estradiol (17β) |
| estriol | estriol azobenzoic acid of Example 2 | estriol |
| estrone | estrone azobenzoic acid of Example 3 | estrone |
| insulin* | insulin azobenzoic acid of Example 9 | insulin |
| tetrahydrocannabinol(THC) | THC azobenzoic acid of Example 11 | THC |
| thyrotropic releasing hormone (TRH) | TRH azobenzoic acid of Example 11 | TRH |

* Molar ratio of 1:25 antibody to antigen derivative used in place of 1:6.

Another immunofluorescent assay forming an embodiment of this invention involves fluorescence enhancement of a fluorescent hapten or antigen derivative of this invention.

This enhancement assay comprises an immunofluorescent method of assaying quantitatively for compounds of structures (I), and (I), herein, which comprises producing a mixture, suitable for fluorometric assay, of (1) a sample to be analyzed, generally from body fluid (although any sample source can be empolyed) and containing the compound under assay, (2) a known quantity of an antibody which is specific for the compound to be assayed, and (3) a known quantity of a hapten or antigen* derivative, possessing an absorbance spectrum (345±10 nanometers) corresponding to the emission spectrum of the antibody, and which is homologous to said assay compound (that is, sharing immunochemical specificity) so as to bind with said antibody competitively; and analyzing said mixture for fluorescence enhancement of the hapten or antigen derivative.
* fluorescent Exemplary of the compounds which can be assayed are the following:

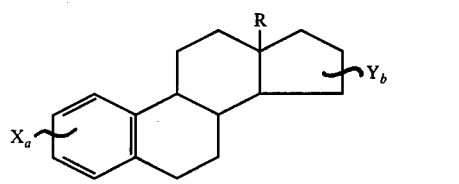
(1)

wherein X, Y, R, $a$ and $b$ are as previously defined;

(2) psychomimetic agents as exemplified by the amphetamines, meperidine, mescaline or tetrahydrocannabinol, i.e. the active constituent of marihuana (hashish);

(3) a catecholamine, as defined before;
(4) a polypeptide, as previously defined;
(5) diethylstibestrol;
(6) a Δ,4,5-steroid as defined before; and
(7) chlortetracycline, tetracycline and chloramphenicol.

The hapten or antigenic derivatives which can be employed for enhancement of their fluorescence by the antibody are typified by the structures III, V, VI and VII; VII, IX and X; III, V, VI and VII; I–III; I–VI, and III–VI herein. Of these, structures I–III, III–V, and III–V, are preferred because they are highly fluorescent and because their excitation spectra optimally overlap the emission spectrum of the antibody.

The assay for fluorescence enhancement is as follows:

A. Establishment of Standard Curve For Sample to be Assayed

One ml of fluorescent hapten or antigen derivative (1 × $10^{-11}$ moles per ml) is added to each of a series of 30 test tubes. To each one of the tubes is also added 1 ml containing concentrations of purified antibody starting with the first tube with a concentration of 1 × $10^{-11}$ moles per ml of antibody up to the last tube which contains 30 × $10^{11}$ moles per ml of antibody. Then an optimal mixture, (e.g. 1 × $10^{-11}$ M/ml) hapten or antigen derivative and 6 × $10^{-11}$ M/ml anitbody, are interacted with an ml of competing underivatized hapten, i.e. assay compound, in increasing concentrations (e.g. 1–10× $10^{-11}$ M/ml). This mixture is allowed to incubate for 10 minutes to 12 hours at ambient temperature and is then read in a spectrophotofluorometer for fluorescence enhancement. Standard tubes contain an equivalent concentration, either of antibody or of derivative hapten diluted in buffer, in the same concentration present when antibody and derivative hapten are mixed together. Excitation is set at 280 nanometers or 340 nanometers and emission read at 420±10 nanometers. The sum of the fluorescence emission for hapten alone at a set concentration and for antibody alone at a set concentration are added. This sum is equal to 100% fluorescence. The actual fluorescence intensity observed upon interaction of antibody and derivatized hapten will read greater than 100% because of enhancement as a result of the binding of the derivative hapten or antigen to the antibody. With increasing concentration of antibody the observed fluorescence increases until hapten-antibody interaction (or binding) is completed. The difference between the fluorescence of the completely interacted hapten-antibody mixture and the sum of the fluorescence of hapten and antibody alone constitutes the percent of enhancement. The percent of enhancement is proportional to the relative concentration of hapten derivative and antibody.

In assaying a sample of underivatized hapten or antigen, an optimal standard ratio of derivatized hapten and antibody (e.g. 1:5–10) is selected for use in testing the underivatized sample. The latter (e.g. estradiol) in increasing concentrations per ml, competes with the fluorescence hapten or antigen derivative for binding with a given amount of antibody and will inhibit the enhancement phenomenon by antibody bound thereto. The percent of decrease in fluorescence enhancement of hapten or antigen derivative caused by binding of antibody with underivatized hapten or antigen sample is directly proportional to the concentration of the underivatized hapten or antigen. The relationship is rendered linear. The more competing unaltered hapten or antigen present in the solution, the less fluorescence enhancement is caused by the antibody. Hence a standard curve can be drawn for an unknown solution.

B. Assay for Underivatized Hapten or Antigen

The solution containing the sample (i.e. underivatized hapten or antigen as previously described) can be a neutral aqueous solution or body fluid (e.g. serum, urine, amniotic fluid, or tissue extract).

To establish the concentration of the unknown in the body fluid the fluorescence intensity of the sample mixture (containing antibody, derivatized hapten or antigen, and the unknown) is compared with the aforementioned standard curve. The control for such assay is body fluid known to contain no underivatized hapten or antigen.

Thus in carrying out the assay a sample of body fluid is obtained and is added (after solids are removed by centrifugation) in dilution to a standard mixture of antibody and derivatized homologous hapten or antigen, the former preferably being present in slight excess (e.g. 5:1). The resulting solution is allowed to incubate at ambient temperature for about 15 minutes to 12 hours. Thereafter the fluorescence of the resulting mixture is determined, generally by a spectrophotofluorometer. The reading from this instrument is compared with the standard curve for the compound under assay and translated to the concentration of sample compound present (mg/ml).

Example 13 illustrates the fluorescence enhancement assay of this invention for quantitation of a variety of underivatized haptens or antigens.

EXAMPLE 13

An aliquot (1-10 ml) of blood is obtained from a patient. Solids are removed by centrifugation. The clear serum is added to a standard mixture of antibody and derivatized homologous hapten or antigen (molar ratio 6:1 antibody to hapten). The resulting mixture is incubated at ambient temperature for about 15 minutes. Thereafter the fluorescence of the resulting mixture is measured in an Aminco-Bowman spectrophotofluorometer (corrections being made for contribution of buffer and non-specific serum contents as established by the controls). The measured fluorescence intensity at 340 nanometers excitation and 420 nanometers emission is compared with the standard curve for the compound under assay and thereby translated into the concentration of sample compound present.

The following Table 3 sets forth the constituents used in each assay for the indicated sample compound in accordance with the method of this example.

TABLE 3

| | FLUORESCENCE ENHANCEMENT | |
|---|---|---|
| Sample to be Assayed | Enhanced Hapten or Antigen derivatives | Enhancing Antibody |
| estradiol (17β) | estradiol azobenzoic acid of Example 1B | estradiol (17β) |
| " | estradiol hydrazobenzoic acid of Example 1C | " |
| " | amino estradiol of Example 1C | " |
| estriol | estriol azobenzoic acid of Example 2B | estriol |
| " | estriol hydrazobenzoic acid of Example 2C | " |
| " | amino estriol of Example 2C | " |
| estrone | estrone azobenzoic acid of Example 3B | estrone |
| " | estrone hydrazobenzoic acid of Example 3C | " |
| " | amino estrone of Example 3C | " |
| insulin* | insulin azobenzoic acid of Example 9A | insulin |
| " | hydrazoinsulin benzoic acid of Example 9B | " |
| " | amino insulin of Example 9B | " |
| tetrahydrocannabinol (THC) | THC azobenzoic acid of Example 11 | THC |
| " | THC hydrazobenzoic acid | " |
| " | amino THC | " |
| thyrotropic | | |

TABLE 3-continued

| | FLUORESCENCE ENHANCEMENT | |
|---|---|---|
| Sample to be Assayed | Enhanced Hapten or Antigen derivatives | Enhancing Antibody |
| releasing hormone (TRH) | THR azobenzoic acid of Example 11 | TRH |
| " | TRH hydrazobenzoic acid | " |
| " | amino TRH | " |

* Molar ratio of 25:1 antibody to antigen derivative used in place of 6:1.

Another assay method of this invention comprises radioimmune immuno methods to assay quantitatively for compounds of structures (I), and (I) herein which comprises producing a mixture, suitable for isotope counting assay of (1) a sample to be analyzed, generally from body fluid (although any sample source can be employed), (2) a known quantity of an isotopically labeled (e.g. $I^{125}$)* antibody which is specific for the compound to be assayed and (3) a hapten or antigen derivative, insolubilized by covalent linkage to a solid organic (e.g. cellulose derivative) or inorganic (e.g. amino glass) matrix (pretreated e.g. with albumin to minimize non-specific adsorption). The hapten or antigen derivative is homologous to said assay compound (that is, shares immunochemical specificity) so as to bind with said antibody competitively. The supernatant from this mixture is analyzed for diminution of counts per minute after incubation. This approach is unique and minimizes nonspecific adsorption as compared with present radioimmune assays.

* Other labels can be used, e.g. $I^{131}$, $C^{14}$, $I^{127}$, $S^{35}$

Exemplary of the compounds which can be assayed are the following

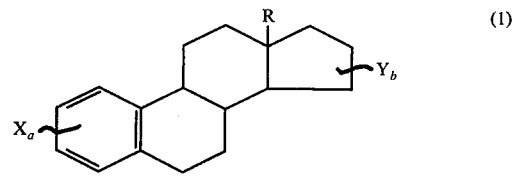

wherein X, Y, R, $a$ and $b$ are as previously defined;

(2) psychotomimetic agents as exemplified by the amphetamines, meperidine, mescaline or tetrahydrocannabinol, i.e. the active constituent of marihuana (hashish);

(3) a catecholamine, as defined before;

(4) a polypeptide, as previously defined;

(5) diethylstibestrol;

(6) a Δ4,5-steroid as defined before; and (7) chlortetracycline, tetracycline and chloramphenicol.

The hapten or antigenic derivatives are covalently coupled to the solid matrix to render them insoluble. These insoluble derivatives compete with homologous underivatized hapten or antigen in the sample for antibody. The haptenic or antigenic portion of these coupled derivatives are typified by the above compounds (1-7). Illustrative of the coupled derivatives are structures I-IV, hereof.

1. The radioimmune assay using solid phase covalently bonded hapten or antigen is as follows:

A. Establishment of Standard Curve

One ml of radioisotopic labeled* antibody (e.g. $I^{125}$) diluted 1:100 – 1:20,000 is added to each of a series of 20 tubes prepared for isotope counting. To each one of the tubes is also added 1 ml containing 1-10 mg of solid matrix (e.g. glass beads) covalently bound to hapten or antigen. An optimal mixture is selected (i.e. one in which 40-50% of total counts are removed from the liquid phase by insolublized derivative. The mixture is interacted with competing underivatized hapten, i.e. assay compound, in increasing concentrations (e.g. 10-100 pikograms/ml). This mixture is allowed to incubate for 8 to 12 hours at 5°-37°. After separation of clean, insolubilized material, radioactive counts of solid (or liquid) phases are measured in a scintillation counter. Control tubes contain inert IgG, uncoupled solid matrix, heterologous insolubilized hapten or antigen in the same concentrations.

* Labeling is exemplified by chloramine T method while antibody binding sites are protected on a solid immuno adsorbant. Counts per minute are $10^8$ or more in 0.20-0.50 μg-ml. Antibody is purified by chromatography.

In assaying a sample of underivatized hapten or antigen, optimally labeled (e.g. $10^8$ counts per minute in 0.20 μg/ml) antibody, purified and diluted (e.g. 1:10,000), selected for use in testing the soluble underivatized sample (hapten or antigen excess). The latter (e.g. estradiol), in increasing concentrations per ml, competes with insolubilized hapten or antigen derivative for binding with a given amount of labeled soluble antibody, will diminish the counts per minute (CPM) removed by insolubilized hapten and increase the CPM remaining in the aqueous phase (by binding with antibody). The percent of increase of CPM in the aqueous phase is directly proportional to the concentration of the underivatized hapten or antigen in test sample. The relationship is rendered linear. The more competing unaltered hapten or antigen present in the test solution, the less counts are removed by the covalently insolubilized hapten or antigen. Hence a standard curve is drawn for the test compound.

B. Assay for Underivatized Hapten or Antigen

The solution containing the sample (i.e. underivatized hapten or antigen as previously described) can be neutral aqueous solution or a body fluid (e.g. serum, urine, amniotic fluid or tissue extract).

The concentration of the unknown in the body fluid is established by counting radioactivity of the aqueous phase of the sample mixture after competition with insolubilized hapten or antigen covalently coupled to glass beads, for binding with labeled antibody. CPM are compared with the aforementioned standard curve. The control for such assay is body fluid known to contain no underivatized hapten or antigen.

Thus in carrying out the assay a sample of body fluid is obtained and is added (after solids are removed by centrifugation) in dilution to a standard mixture of antibody and insolubilized homologous hapten or antigen, the latter being present in a molar excess. The resulting solution is allowed to incubate at 5°-37° C for 8-12 hours. Thereafter the radioactive counts in the aqueous phase is determined, generally by a scintillation counter. The reading obtained by this instrument is compared with the standard curve for the compound under assay and translated to the concentration of sample compound present (nanograms or pikograms/ml).

Another embodiment is a radioimmune assay using solid phase covalently bonded antibody wherein the isotope (label)* (e.g. $I^{125}$) is on the protein carrier moiety of the hapten-protein conjugate, rather than on the hapten moiety of prior art assays. This technique diminishes radioisotopic damage to functional groups and prevents steric hindrance.

* Labeling is exemplified by chloramine T method while antibody binding sites are protected on a solid immuno adsorbant. Counts per minute are $10^8$ or more in 0.20-0.50 μg-ml. Antibody is purified by chromatography.

Such an approach is novel and also includes isotopically labeling haptenless protein carriers such as any polyaminoacid in solution, or as a colloidal suspension, containing one or more available functional groups for coupling to an underivatized or derivatized hapten or antigen of this invention. Exemplary are groups selected from hydroxy, amino (containing at least one reactive hydrogen), hydrogen, carboxyl, carboxy, sulfhydryl, nitro, nitroso, thio, alkoxy, aryloxy, thioalkoxy, thioaryloxy, halo, disulfide, heterocyclic groups such as histidyl, and carbocyclic, such as tyrosyl. Exemplary of the polyamino acids are polypeptides, such as polytyrosine, or any polypetide produced, for example, by reacting an amino acid with a carboxylic acid by carbodiimide condensation. Generally, any polyamino acid can be employed, provided that in addition to the above functional groups for coupling to the hapten or antigen, sufficient sites for labeling with an isotope, such as $I^{125}$, $I^{131}$, or $H^3$ are present. However, any isotope can be used which exhibits high specific activity and efficiency. Other polymeric organic or inorganic carriers can be employed, provided that they have suitable reactive groups available for coupling as described above. Exemplary of these carriers are the polysiloxanes, polymeric silica derivatives (for example U.S. Pat. No. 3,519,538), organic polymers, such as polyetheylene, polypropylene, and other conventional polymers known to the art. The only limitations on the carriers to be employed in this embodiment are: (1) available functional groups for coupling to the underivatized or derivatized antigen homologous to the compound under assay, (2) suitable for isotopic labeling, and (3) stable under the conditions of the assay. When employing radioactive iodine as the isotope label, it is preferred to employ a polyamino acid containing one or more tyrosyl groups. The polypeptides can be as small as a dipeptide, but, generally, the molecular weights of the polyamino acids exceed 300 and may be as much as 7 million, or more. Further exemplary of the carrier moieties are the proteins described supra at pages 7 and 8.

2. Radioimmune assay using labeled carrier protein of hapten-protein conjugate:

The soluble, labeled conjugate competes with underivatized hapten or antigen in test fluid for purified antibody (unlabeled) (or labeled with a different isotope) which is insolubilized by covalent linkage to a solid matrix (e.g. glass beads). (See U.S. Pat. No. 3,519,538, for example)

A. Selection of Antibody Dilution

Utilizing a standard dilution of hapten-protein conjugate (total $10^8$ CPM in 0.2 ug/ml), the insolubilized antibody is diluted 1:10-10,000 in a series of 50 tubes. A tube in which 40-60% of the total counts/min. are removed by insolubilized antibody is selected as containing the optimal ratio of antibody and marker antigen.

B. Standard Curve

The optimal mixture as selected from procedure A above is used in a series of tubes (e.g. 1-20) and into each of which is added a known amount of an underivatized hapten or antigen in nanogram or pikogram increments. After incubation for 8-12 hours at 5°-37° C, CPM are determined. The more unlabeled hapten or antigen in a given tube the more counts are retained in the aqueous phase. The standard curve is rendered linear.

C. Assay for Underivatized Hapten or Antigen

The solution containing the sample (i.e.) underivatized hapten or antigen as previously described) can be a neutral aqueous solution or body fluid (e.g. serum, urine, amniotic fluid, or tissue extract).

To establish the concentration of the unknown hapten or antigen in the body fluid, the radioactivity of the aqueous phase of the sample mixture, containing unknown hapten (or antigen), and hapten-protein conjugate (with the marker on the carrier protein) is compared, after interaction with purified antibodies covalently coupled to glass beads, with the aforementioned standard curve. The control for such assay is a liquid or body fluid known to contain no underivatized hapten or antigen.

Thus in carrying out the assay a sample of liquid or body fluid is obtained and is added (after solids are removed by centrifugation) in dilution to a standard mixture of insolubilized antibody covalently coupled to glass beads andmarker protein - hapten conjugate. Hapten or antigen are in molar excess over antibody. The resulting solution is allowed to incubate at 5°-23° C for 8-12 hours. Thereafter the radioactive counts in the aqueous phase are determined, generally by a scintillation counter. The reading from this instrument is compared with the standard curve for the compound under assay and is translated to the concentration of the compound present in nanograms or pikograms per ml.

The foregoing assay can be repeated with the exception that a haptenless protein carrier (as defined above) is first isotopically labeled, followed by coupling to the desired hapten or antigen in accordance with this invention, rather than labeling the derivatized hapten or antigen.

The following Example 14 further illustrates the preparation of the novel steroid-protein conjugates of this invention. In this example p-aminobenzoic acid (PABA) is rapidly diazotized in the presence of an estrogen whose reactive phenolic C-3 function permits entry in the A ring at position 2 or 4 (but not both) by the distal nitrogen atom. The resulting azosteroid is coupled to a protein through the azobenzoyl carboxyl by condensation with a soluble carbodiimide, 1-cyclohexyl-3-(2-morpholinoethyl)carbodiimide metho-p-toluene sulfonate.

EXAMPLE 14

PABA (137 mg) is dissolved in 1.0 N HCl (10 ml). The beaker is cooled by crushed ice for 5 minutes and 20% $NaNO_2$ (100 mg) is added while stirring. The temperature is not permitted to rise above 5° C. When all nitrite has been added (slight excess) a pale blue spot develops rapidly on testing with wetted starch-iodide paper. Excess $NaNO_2$ is removed by sulfamic acid. The solution became clear yellow. Diazotization requires 15 minutes, the pH never exceeding 1.0.

Crystalline estradiol, estriol or estrone (100 mg) is dissolved in 90% methanol (25 ml). Diazotized PABA is added dropwise, the pH being maintained at 10-11. The final mixture is acidified with 0.1 N HCl to remove excess (soluble) PABA and side reaction products. The azosteroid precipitate is recovered, triturated and redissolved in 0.1 N NaOH. Centrifugration removes insoluble unreacted steroid. After repeating the acid and base cycle once, the azosteroid is extracted into a mixture of benzene and methanol (4:1) which is evaporated to dryness.

Crystalline azosteroid (25 mg) is added to a 1% saline solution containing 0.1 M carbodiimide (100 mg) and KLH (keyhole limpet hemocyanin) or IgG (human immune globulin) (250 mg). The mixture is stirred until azosteroid has coupled and is dialyzed for 2-3 days at 3° C in 0.5 M sodium carbonate, pH 8.2 until color no longer appears in dialysis solution. A final dialysis is performed against 0.9% NaCl for 24 hours. The preceding steps remove unreacted steroid and derivative molecules. Insoluble protein is removed by centrifugation. Protein determination is made on the colored superanatant containing steroid-protein conjugate. The concentration is adjusted to approximately 1% by spectral measurement at 280 m$\mu$.

Analysis of azobenzoyl derivatives (i.e. steroid-azobenzoic acid)

Samples are initially examined by thin layer chromatography (TLC). Glass slides coated with silica G are spotted and developed with chloroform: ethyl acetate: acetic acid (40:60:50). Then slides are heated 10 minutes at 110° C, sprayed with concentrated $H_2SO_4$ and observed under ultraviolet light while charring. For quantitative spectral analyses and immunization samples are further purified by preparative TLC on 10 × 14 cm glass plates coated with silica G. Development in one direction is done with ether:methanol:acetic acid (94:5:1). Material migrating as reference standard is scraped from the plate and recovered by original solvent (10 times volume). The structure of the azoestradiol, azoestriol, azoestrone, and the corresponding fluorescent hydrazo and amino steroids are confirmed by mass spectroscopy and nuclear magnetic resonance. Azo derivatives have been hydrolyzed intact from protein conjugates and quantitated thus confirming structures of azoestradiol-KLH, azoestriol-KLH, azoestrone-KLH and the corresponding steroid-IgG conjugates. These structures are set forth in Table 4.

TABLE 4

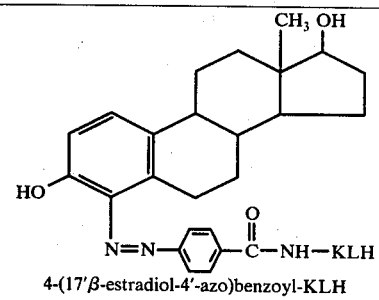

4-(17'β-estradiol-4'-azo)benzoyl-KLH

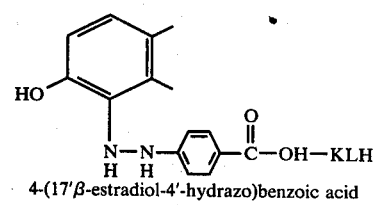

4-(17'β-estradiol-4'-hydrazo)benzoic acid

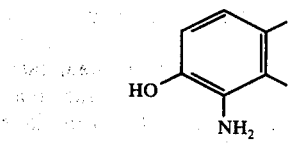

TABLE 4-continued 4-amino-17'β-estradiol

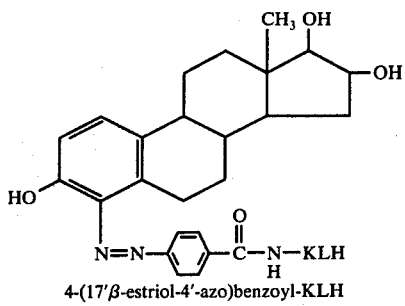
4-(17'β-estriol-4'-azo)benzoyl-KLH

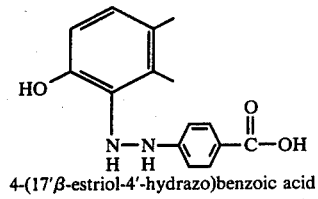
4-(17'β-estriol-4'-hydrazo)benzoic acid

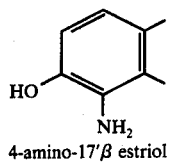
4-amino-17'β estriol

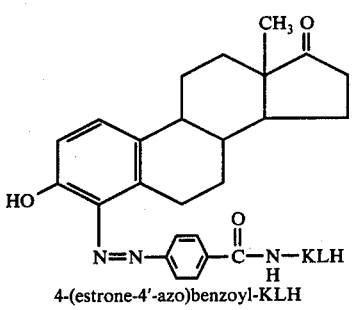
4-(estrone-4'-azo)benzoyl-KLH

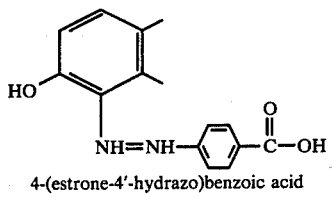
4-(estrone-4'-hydrazo)benzoic acid

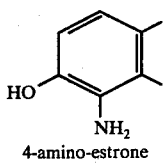
4-amino-estrone

Absorption spectra of derivatives and conjugates are measured on a Cary recording spectrophotometer using rectangular cells of 10mm light path. Difference spectra are obtained with 0.1 cm cell paths. An Aminco-Bowman spectrophotofluorometer operated with a number 5 slit arrangement yielding a spectral band pass of 22 mu is used for initial excitation and emission measurements and a 5233253 arrangement (band pass=11 mu) for enhancement readings. A further diminution cuts the signal without increase in resolution.

Example 15 demonstrates the use of the foregoing steroid-protein conjugates prepared in accordance with Example 14 to immunize a host. Production of antibody specific to the particular steroid-protein conjugate administered is also shown. In Example 15 the estradiol-KLH conjugate is employed; however, any of the conjugates of this invention can be used in a similar manner to produce antibody specific for the homologous steroid.

EXAMPLE 15

Immunization

Adult New Zealand rabbits are immunized with pure azoestradiol-KLH conjugates. Intravenous injections are done twice weekly for two weeks, the total dose is 30 mg. Blood is drawn by cardiac puncture 1 and 2 weeks after the last injection. (Effective antisera are also raised by a single subcutaneous injection of complete Freunds adjuvant containing 2.5 ml of 1% pure steroid-protein conjugate, blood being obtained 21-28 days later.)

Antibody Purification

Aminoethylcellulose (500 mg) is coupled through its amino groups Weliky et al, Immunochem., 1, 219 (1964) to homologous or heterologous azosteroid (100 mg) in the presence of N-N'-dicyclohexylcarbodiimide as described above for synthesis of steroid-protein conjugates. Antibodies are dissociated by 1.0N HAC (acetic acid) 3M urea from the solid matrix used as a slurry or in a reusable column. Amino derivatized glass has also been used for such a matrix.

Immunological Analysis

Azosteroid-KLH antisera are tested against azosteroids coupled to human IgG. Quantitative precipitin tests are done in duplicate. Tubes containing increasing concentrations of antigen are incubated with 0.25-0.50 ml antiserum diluted 1:1 at 38° C for 1 hour and at 4° C for 60 hours. Precipitates are washed three times with cold saline, dissolved in 0.5 N NaOH and the total protein determined by the Lowry method i.e. see Lowry et al., J. Biol. Chem., 153, 265 (1951). Quantitative absorption experiments are done in the same manner. Increasing concentrations of steroid-IgG conjugates are used to absorb antisteroid-KLH sera and the latter are then tested with a standard concentration of homologous conjugate. For immunoelectrophoresis glass slides are layered with two ml of 1.0% agar in 0.075 M veronal buffer, pH 8.6 (B2 buffer, Beckman Instruments). A total of 50 mA is delivered to six slides which are subsequently developed in a moist chamber for 12-72 hours at room temperature. Microimmunodiffusion experiments are done placing 1.5 cm square templates upon 0.5 ml agar, see Gross et al., Nature, 219, 758 (1968). Quenching of antibody fluorescence by azosteroid haptens is determined at an excitation wave length of 280 nm and emission determined at a wave length of 350 nm. Enhancement of hapten fluorescence by antibody is measured at wave lengths of 336 nm for excitation and 420 nm for emission.

Absorption Spectra

Initial spectra obtained for crude azosteroids determines the extent of substitution in proteins. Measurements are obtained before conjugation and after removal of azo derivatives from protein carriers by alkaline hydrolysis, see Gross et al., Immunochem., 5, 55 (1968). The azosteroid derivatives (i.e. azoestradiol, azoestriol and azoestrone) have absorption maxima of 350-364 mu in methanol and 344 mu in bicarbonate or phosphate buffer, pH 8.6. The molar extinction coefficient of estradiol azobenzoic acid (AED) chromophore is unchanged when coupled to protein, increased absorption by conjugate over that of untreated protein at 350 mu divided by the extinction coefficient yields the concentration of steroid residues. Subtraction of the latter from concentration of conjugate gives the molar concentration of protein constituent. Molar ratios calculated from spectral curves range from 4-30 and are similar to those derived from TLC.

Thin Layer Chromatography (TLC)

The single qualitative difference between crude and purified azosteroids migrating on TLC is the presence of a substantial amount of material remaining at the origin of the former and none at the origin of the latter. In the chromatography of both only one spot migrates. Its rate is almost as rapid as reference standard steroids ($R_s = 0.87(8)$). Relative mobilities of azoestradiol and azoestriol are identical to those of untreated estradiol and estriol standards. Bright yellow fluorescence of azosteroid after spraying with $H_2SO_4$ matches that of standard steroid and remains entirely superimposed on the spot occupied by migrating azo derivative seen under visible light. Colored material retained at origin in TLC of crude samples does not fluoresce. Progesterone and testosterone treated with diazotized PABA migrate separately and in advance of the orange colored azo spot. Additional purification is achieved by recrystallization.

* However, coupled product is also produced.

Treatment of steroid-proteins with 1.0 N NaOH at 100° C for 2 hours recovers hydrolytic azosteroids which migrate and fluoresce exactly as the original derivatives. Results indicate no major alteration in the steroid as a result of coupling. TLC reveals the minimum number of steroid residues per molecule of protein carrier (Table 1).

TABLE 1

Molar ratios of representative steroid-protein conjugates

| Steroid | Protein KLH | IgG |
|---|---|---|
| estradiol | 29 | 19 |
| estriol | 25 | 20 |
| estrone | 27 | 5 |

Purification of Azoestradiol Antibodies

From 200 mg matrix 0-300 ug (5.0 ml serum) antibody is recovered by dilute acid (1.0N HAC or 0.1 N HCL). Average recovery is 25%. Urea (3.8M), pH 3.2-4.0 can also be used for dissociation. Measurement of reactivity of recovered proteins indicates specific binding to homologous hapten and to diethylstilbestrol.

Quantitative Precipitation Reactions

Azoestradiol-IgG (20:1 molar ratio) precipitates 220-1200 ug/ml antibody protein. In one anti-AED-KLH serum from the initial group of immunized rabbits, 354 ug/ml antibody is brought down by homologous hapten coupled to human Serum (0.25 ml) is diluted 1:1 and tested against increasing concentrations of IgG conjugates. Total volume is 1.25 ml. Supernatant is not examined. Antigen concentrations are determined spectrally. Although estrone is less highly coupled to carrier IgG than estradiol (Table 1), all dilutions of estrone conjugate fail to precipitate 50% as much antibody as estradiol-IgG. Estriol cross reacts moderately in reactions with crude antibody. IgG standard, IgG treated with diazotized PABA, progesterone (or testosterone) and carbodiimide are negative. Quantitative absorption results with related conjugates indicating specifi-city of crude anti-estradiol-KLH for homologous hapten. Hapten inhibition (of antibody) for precipitin studies, however, are quantitatively unsatisfactory probably because of restricted sensitivity and hapten solubility in neutral aqueous solution.

For higher sensitivity and to calculate precise specificities of steroid-protein interactions fluorescence quenching and enhancement provides a way which does not require drastic physical alteration of the steroid molecule or interfere, with its binding kinetics. Quenching maximum (Q max) is determined experimentally in hapten excess The test values for Q max yield an association constant ($K_o$) in agreement with one derived from equilibrium dialysis (for number of binding sites). However, constants determined by fluorescence quenching (assuming antibody valence of two) are useful when comparing related haptens in a given system.

For measurement of small quantities of hapten bound (either by dilution or lower association constants e.g. with subunits of IgG) we have applied the technique of fluorescence enhancement using a highly fluorescent steroid which acts as a "reporter group" in the study of steroid-protein interactions. High natural fluorescence is induced by reduction of azobenzoyl to hydrazobenzoyl derivatives as previously discussed. Synthesis and characterization are described hereafter. Fluorescence excitation and emission maxima for hydrazoestradiol (HED) are 338 nm and 420-445 nm Fluorescence emission spectra are produced by excitation at a wavelength of 336 m$\mu$. Note the spectral shifts of HED interacting with antibody and normal IgG. HED + antibody (—), HED + normal IgG (- . - .), HED (- . - .), antibody IgG (- - -). The normal rabbit IgG curve coincides with that of antibody. Concentrations for HED ($1 \times 10^{31\ 8}$ M) and proteins ($5 \times 10^{31}$ [M]) are constant in each sample, corrections being made for dilution. Emission curves using an excitation wavelength of 336 nm demonstrate a downward shift of emission and fluorescence enhancement. Similar changes are observed at $10^{31\ 6}$ M.

Quenching of antibody fluorescence by HED measured on the same samples (at the lower concentration) using an excitation wavelength of 284 mu and reading intensity of emission at 350 nm produces curves similar to those of AED.

The chemical changes produced with steroid derivative haptens also are achieved with steroid-protein conjugates. Microgel immunodiffusion performed under nitrogen indicate immunological identity as well as specificity of HED and AED determinants.

Labeling the antibody used in prior art solid phase radioimmune assays, employing an antibody specific for the compound to be analyzed, constitutes another novel embodiment of this invention. These prior art assays are well known and therefore are not described in detail here. Briefly the constituents of such prior art solid phase assays are as follows:

(1) known quantity of labeled assay compound;
(2) known quantity of antibody;
(3) disks (polystyrene);

(4) sample containing unknown amount of assay compound.

In contrast to the prior art method, in the subject embodiment the antibody is labeled, rather than the test compound, and the assay otherwise is conventionally carried out. Such assay results in less damage to the labeled entity and does not damage the test compound.

By virtue of labeling the antibody a higher intensity of radioactivity can be produced to achieve greater sensitivity, spacificity and a shorter incubation period. Thus, a shorter more accurate test is achieved even when compared to modern solid phase assays which have been devised to simplify and shorten the assay as carried out by the double antibody technique.

EXAMPLE 16
4-EPINEPHRINE AZOBENZOIC ACID 0.75 Milliequivalents para-aminobenzoic acid is added to 10 ml of 1N HCl and chilled to 5° C. Sodium nitrite (0.85 milliequivalents) is added, stirred in an ice bath for 20 minutes, pH not exceeding 1 and the mixture tested with starch-iodide paper. Excess nitrite is removed using sulfamic acid. Diazotized para-aminobenzoic acid is added dropwise to an equivalent concentration of epinephrine (0.75 milliequivalents) dissolved in 1/10 molar phosphate buffer, pH 11, containing 10% methanol. After mild acidification the epinephrine azobenzoic acid is extracted and purified by preparative chromatography.

4-EPINEPHRINE HYDRAZOBENZOIC ACID AND AMINOEPINEPHRINE

Purified epinephrineazobenzoic acid (25 mg) (0.15 mg/ml) is dissolved in 0.1 M acidic acid (pH 5.5) containing 30% methanol. An eight-fold molar excess of sodium borohydride is added as a solution in water, the mixture being flushed with nitrogen. Aminoepinephrine and hydrazoepinephrine are separated by extraction and chromatography. The compounds are treated with 2,6 di-tert-butyl p-aerosol (1% by weight of derivative molecules) and desalted by chromatography.

4-EPINEPHRINE AZOBENZOYL-KLH 0.1 molar 1-cyclohexyl-3-(2-morpholinoethyl) carbodiimide metho-p-toluene sulfinate (100mg) in water is added to purified 4-epinephrine azobenzoic acid (25 ). The desired intermediate 0-1,3-dicyclohexyl-2-[4-epinephrine azobenzoyl] pseudourea is thereby produced.

KLH is added to the foregoing mixture. The mixture is stirred until the intermediate azopseudourea has coupled to KLH and is dialyzed for 48 hours in sodium acetate 0.1M, pH 5.4 until color no longer appears in dialysis solution. A final dialysis is performed against distilled water, the conjugate is then lyophilized.

When Example 16 is repeated with the exception that a like amount of immune gamma globulin or bovine serum albumin is substituted for KLH as the protein, the corresponding globulin or albumin conjugates are respectively produced, the reactions proceed through the corresponding intermediate protein-pseudourea.

EXAMPLE 17
4-TRH* AZOBENZOIC ACID 0.75 Milliequivalents para-aminobenzoic acid is added to 10 ml of 1N HCl and chilled to 5° C. Add 0.85 milliequivalents sodium nitrate. Stir in ice bath for 20 minutes, pH not exceeding 1. Test with starch-iodide paper. Excess nitrite is removed withسلfamic acid. Diazotized para-amino benzoic acid is added dropwise to an equivalent concentration of TRH (0.75 milliequivalents) dissolved in 1/10 molar phosphate buffer, pH 11 containing 10% methanol. After mild acidification the TRH azobenzoic acid is extracted and purified by preparative chromtography.
*Thyrotropic releasing hormone

4-TRH HYDRAZOBENZOIC ACID AND AMINO TRH

Purified TRH azobenzoic acid (25 mg) (0.15 mg/ml) is dissolved in 0.1 M acidic acid (pH 5.5) containing 30% methanol. An eight-fold molar excess of sodium borohydride is added as a solution in water, the mixture being flushed with nitrogen. Amino TRH and 4-hydrazo TRH are separated by extraction and chromatography. The compounds are treated with 2,6-di-tert-butyl p-cresol (1% by weight) of derivative molecules) and desalted by chromatography.

4-TRH AZOBENZOYL-KLH 0.1 molar 1-cyclohexyl-3-(2-morpholinoethyl) carbodiimide metho-p-toluene sulfonate (100 mg) in water is added to purified 4-TRH azobenzoic acid (25 mg). The desired intermediate 0-1,3-dicyclohexyl-2-[4-TRH-azobenzoyl] psuedourea is thereby produced.

KLH is added to the foregoing mixture. The mixture is stirred until the intermediate azopseudourea has coupled to KLH and is dialyzed for 48 hours in sodium acetate 0.1M, pH 5.4 until color no longer appears in dialysis solution. A final dialysis is performed against distilled water, the conjugate is then lyophilized.

When Example 17 is repeated with the exception that a like amount of immune gamma globulin or bovine serum albumin is substituted for KLH as the protein, the corresponding globulin or albumin conjugates are respectively produced, the reactions proceed through the corresponding intermediate protein-pseudourea.

EXAMPLE 18
4-THC AZOBENZOIC ACID 0.75 Milliequivalents para-aminobenzoic acid is added to 10 ml of 1N HCl and chilled to 5° C. Add 0.85 milliequivalents sodium nitrite. Stir in ice bath for 20 minutes, pH not exceeding 1. Test with starch-iodide paper. Excess nitrite is removed with sulfamic acid. Diazotized para-aminobenzoic acid is added dropwise to an equivalent concentration of THC (0.75 milliequivalents) dissolved in 1/10 molar phosphate buffer, pH 11 containing 10% methanol. After mild acidification the THC azobenzoic acid is extracted and purified by preparative chromatography.
*Tetrahydrocannabinol

4-THC HYDROAZOBENZOIC ACID AND AMINO THC

Purified THC azobenzoic acid (25 mg) (0.15 mg/ml) is dissolved in 0.1 M acidic acid (pH 5.5) containing 30% methanol. An eight-fold molar excess of sodium borohydride is added as a solution in water, the mixture being flushed with nitrogen. Amino TCH and 4-hydrazo TCH are separated by extraction and chromatography. The compounds are treated with 2,6 di-tert-butyl p.- cresol (1% by weight of derivative molecules) and desalted by chromatography.

4-THC AZOBENZOYL-KLH 0.1 molar 1-cyclohexyl-3-(2-morpholinoethyl) carbodiimide metho-p-toluene sulfonate (100 mg) in water is added to purified 4-THC azobenzoic acid (25 mg). The desired intermediate 0-1,3-dicyclohexyl-2-[4-THC-azobenzoyl] pseudourea is thereby produced.

KLH is added to the foregoing mixture. The mixture is stirred until the intermediate azopseudourea has coupled to KLH and is dialyzed for 48 hours in sodium acetate 0.1M, pH 5.4 until color no longer appears in dialysis solution. A final dialysis is performed against distilled water, the conjugate is then lyophilized.

When Example 18 is repeated with the exception that a like amount of immune gamma globulin or bovine serum albumin is substituted for KLH as the protein, the corresponding globulin or albumin conjugates are respectively produced, the reactions proceed through the corresponding intermediate protein-pseudourea.

When any of the foregoing Examples 1–4 is repeated with the exception that an equivalent amount of any of the following steroids is substituted for the steroid used in said examples the corresponding steroid azobenzoic acid, steroid hydroazobenzoic acid, amino steroid and steroid azobenzoyl-protein are produced: equiline (1,3,5,7-estrotetroen-3-ol-17-one; equiline glycol 1,3,5-estratrien-17-one-3,7,8-triol; equilenin, 1,3,5:10,6,8-estropentoen-3-ol-17-one; dihydroequinline-17 alpha; dihydroequinlenine-17 alpha; 4-methoxy-estrone; 2-methoxy-estrone; 2-methoxy-estradiol; 16-oxo-estrone; 16 alphahydroxy-estrone; 16 beta-hydroxy-estrone; 18-hydroxy-estrone; 16-oxo-estradiol-17 beta; 6-oxo-estradiol-17-beta; 16-epiestriol (16 beta, 17 beta); 17-epiestriol (16 alpha, 17 beta); 16-epiestriol (16 beta, 17 beta); 17-epiestriol (16 alpha, 17 beta); estradiol 17 beta-cyclopentane propionate; 16 alpha, 17 beta-estriol. Then steroid azobenzoic acid products thus produced can be substituted in equivalent amounts for the steroid azobenzoic acids of Example 5–8 to produce the corresponding steroid azobenzoyl-protein.

Furthermore, in any of Examples 1–4 an equivalent amount of the following aryloic compounds can be substituted for para aminobenzoic acid to yield the corresponding arylene azo-derivative: p-aminobenzene; p-nitroaminobenzene; p-nitrophenylchloride; p-aminophenylchloride; p-chloroaminobenzene; p-chloroamino benzoic acid; or the meta isomers of the foregoing; or the di- or tri- substituted benzene analogs of the foregoing; or the naphthyl analogs of the foregoing. These steroid azoarylaic acid products can also be substituted for steroid azobenzoic acids of Example 5–8 to produce the corresponding steroid azoaroyl-proteins.

In carrying out the diazotization step in the above reaction sequences I and II, any diazonium salt with diazonium groups attached to aryl can be employed. Also other systems, sustaining a diazonium ion can be used. Exemplary are heterocyclic, or polycyclic nuclei, such as pyridine, pyrazone, triazole, benzyrene, metal chelates [e.g. tri-(acetylacetonate) chronium]; hyponitrite ester (RO—N=N—OR); thio analog of azoxybenzene (RN—S—NR).

I claim:

1. In a quantitative immunoassay for the presence of a target in a sample comprising producing a mixture of the sample, a known quantity of an antibody which is immunologically specific for the target, and a known quantity of a standard immunologically homologous to the target, so as to bind with said antibody competitively, one of said antibody and said standard having a covalently bonded derivative capable of emitting radiation from the mixture, providing for competitive antibody binding to take place and measuring the radiation emitted from a portion of the derivative, which radiation measurement is indicative of the relative proportions of target and standard binding with the antibody, and thus the amount of target present, the improvement comprising employing as the antibody, antibody raised by and specific to the hapten portion of a synthetic antigen comprising a plurality of hapten moieties covalently bound to a carrier, said moieties being immunologically homologous with the target and the hapten being bound by a —N=N— group coupled directly to an otherwise unsubstituted ring atom of the hapten.

2. The immunoassay of claim 1 wherein the target is a compound selected from the group consisting of estrone, estradiol, estriol, morphine, tetrahydrocannabinol, amphetamine, epinephrine, norepinephrine, a diazepoxide, angiotensin, thyroxin, aldosterone, thyrotropic release hormone, luteinizing hormone, adrenocorticotropin, and testosterone.

3. The immunoassay of claim 1 wherein the carrier is a protein selected from the class consisting of keyhole limpet hemocyanin, bovine serum albumin, and human gamma globulin.

4. In a quantitative immunoassay for the presence of a target in a sample comprising producing a mixture of the sample, a known quantity of an antibody which is immunologically specific for the target, and a known quantity of a standard immunologically homologous to the target, so as to bind with said antibody competitively, one of said antibody and said standard having a covalently bonded derivative capable of emitting radiation from the mixture, providing for competitive antibody binding to take place and measuring the radiation emitted from a portion of the derivative, which radiation measurement is indicative of the relative proportions of target and standard binding with the antibody, and thus the amount of target present, the improvement comprising employing as the antibody, antibody raised by and specific to an antigen of formula:

$$\text{carrier}-\text{Ar}-\text{N}=\text{N}-\text{hapten}]_n$$

in which "carrier" is an immunogenic carrier; Ar is an arylene radical to which the immunogenic carrier is linked through a connective group; the hapten is immunologically homologous to the target when coupled to the carrier through the arylene and azo groups, and has a ring with an unsubstituted ring atom bonded directly to the azo group; and $n$ is an integer not exceeding the number of functional moieties available on the carrier to partake in forming said connective group.

5. The immunoassay of claim 4 wherein the target is a compound selected from the group consisting of estrone, estradiol, estriol, morphine, tetrahydrocannabinol, amphetamine, epinephrine, norepinephrine, a diazepoxide, angiotensin, thyroxin, aldosterone, thyrotropic release hormone, luteinizing hormone, adrenocorticotropin, and testosterone.

6. The immunoassay of claim 4 wherein the carrier is a protein selected from the class consisting of keyhole limpet hemocyanin, bovine serum albumin, and human gamma globulin.

7. The immunoassay of claim 1 wherein the synthetic antigen employed is one with a purity of at least 98%.

8. The immunoassay of claim 1 wherein the synthetic antigen is an antigen prepared by a method including coupling of an immunogenic carrier with an azo-hapten compound and in which said azo-hapten compound has a purity of at least 98%.

9. The immunoassay of claim 4 wherein the synthetic antigen employed is one with a purity of at least 98%.

10. In a quantitative radioimmune assay for the presence of a target in a sample comprising providing a mixture of the sample, a known quantity of a antibody which is immunologically specific for the target, and a known quantity of a standard immunologically homologous to the target so as to bind with said antibody competitively, one of the antibody and the standard having a covalently bonded radioisotopic derivative, providing for competitive antibody binding, separating bound derivative compound from unbound derivative compound and measuring the radiation emanating from one of said separated and unseparated derivative compounds to indicate the proportion of antibody bound to the standard, and thus the amount of target present, the improvement which comprises employing as the antibody, antibody raised by and specific to the hapten portion of a synthetic antigen comprising a plurality of hapten moieties covalently bound to a carrier, said moieties being immunologically homologous with the target and the hapten being bound by a —N=N— group coupled directly to an otherwise unsubstituted ring atom of the hapten.

11. The immunoassay of claim 10 wherein the target is a compound selected from the group consisting of estrone, estradiol, estriol, morphine, tetrahydrocannabinol, amphetamine, epinephrine, norepinephrine, a diazepoxide, angiotensin, thyroxin, aldosterone, thyrotropic release hormone, luteinizing hormone, adrenocorticotropin, and testosterone.

12. The immunoassay of claim 10 wherein the carrier is a protein selected from the class consisting of keyhole limpet hemocyanin, bovine serum albumin, and human gamma globulin.

13. The immunoassay of claim 10 wherein the synthetic antigen employed is one with a purity of at least 98%.

14. The immunoassay of claim 10 wherein the synthetic antigen is an antigen prepared by a method including coupling of an immunogenic carrier with an azo-hapten compound and in which said azo-hapten compound has a purity of at least 98%.

15. The radioimmune assay of claim 10 wherein the separation is a phase separation, one of the standard and the antibody carrying said radioisotopic derivative and the other being insolubilized.

16. The radioimmune assay of claim 10 wherein the radioisotopic derivative is covalently bound to one of the antibody and the carrier portion of the standard, the standard being a hapten-carrier conjugate.

17. In a quantitative radioimmune assay for the presence of a target in a sample comprising providing a mixture of the sample, a known quantity of an antibody which is immunologically specific for the target, and a known quantity of a standard immunologically homologous to the target so as to bind with said antibody competitively, one of the antibody and the standard having a covalently bonded radioisotopic derivative, providing for competitive antibody binding, separating bound derivative compound from unbound derivative compound and measuring the radiation emanating from one of said separated and unseparated derivative compounds to indicate the proportion of antibody bound to the standard, and thus the amount of target present, the improvement which comprises employing as the antibody, antibody raised by and specific to an antigen of formula:

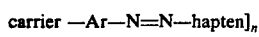

$$\text{carrier} - Ar - N = N - \text{hapten}]_n$$

in which "carrier" is an immunogentic carrier; Ar is an arylene radical to which the immunogenic carrier is linked through a connective group; the hapten is immunologically homologous to the target when coupled to the carrier through the arylene and azo groups, and has a ring with an unsubstituted ring atom bonded directly to the azo group; and $n$ is an integer not exceeding the number of functional moieties available on the carrier to partake in forming said connective group.

18. The immunoassay of claim 17 wherein the target is a compound selected from the group consisting of estrone, estradiol, estriol, morphine, tetrahydrocannabinol, amphetamine, epinephrine, norepinephrine, a diazepoxide, angiotensin, thyroxin, aldosterone, thyrotropic release hormone, luteinizing hormone, adrenocorticotropin, and testosterone.

19. The immunoassay of claim 17 wherein the carrier is a protein selected from the class consisting of keyhole limpet hemocyanin, bovine serum albumin, and human gamma globulin.

20. The immunoassay of claim 17 wherein the synthetic antigen is an antigen prepared by a method including coupling of an immunogenic carrier with an azo-hapten compound and in which said azo-hapten compound has a purity of at least 98%.

21. The radioimmune assay of claim 17 wherein the separation is a phase separation, one of the standard and the antibody carrying said adioisotopic derivative and the other being insolubilized.

22. The radioimmune assay of claim 17 wherein the radioisotopic derivative is covalently bound to one of the antibody and the carrier portion of the standard, the standard being a hapten-carrier conjugate.

* * * * *